US012678291B2

(12) United States Patent
Miller et al.

(10) Patent No.: US 12,678,291 B2
(45) Date of Patent: Jul. 14, 2026

(54) 3D PRINTED METAL CORPECTOMY DEVICE WITH STRUCTURAL AND ENDPLATE LATTICE STRUCTURES

(71) Applicant: Warsaw Orthopedic, Inc., Warsaw, IN (US)

(72) Inventors: Keith E. Miller, Oxford, MS (US); Julien J. Prevost, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 19/257,734

(22) Filed: Jul. 2, 2025

(65) Prior Publication Data

US 2026/0007525 A1 Jan. 8, 2026

Related U.S. Application Data

(60) Provisional application No. 63/668,471, filed on Jul. 8, 2024.

(51) Int. Cl.
A61F 2/44 (2006.01)
A61F 2/30 (2006.01)

(52) U.S. Cl.
CPC .......... A61F 2/442 (2013.01); A61F 2/30771 (2013.01); *A61F 2002/30156* (2013.01); *A61F*

*2002/30841* (2013.01); *A61F 2002/3092* (2013.01); *A61F 2002/3093* (2013.01)

(58) Field of Classification Search
CPC .......... A61F 2/44; A61F 2/442; A61F 2/4465; A61F 2/4455; A61F 2/447; A61F 2/30
See application file for complete search history.

(56) References Cited

U.S. PATENT DOCUMENTS

| | | | |
|---|---|---|---|
| 2017/0333205 A1* | 11/2017 | Joly ...................... | A61F 2/4465 |
| 2021/0085481 A1* | 3/2021 | Cain ...................... | A61F 2/4455 |
| 2022/0296386 A1* | 9/2022 | Fang ...................... | B33Y 80/00 |

* cited by examiner

*Primary Examiner* — Christopher J Beccia
(74) *Attorney, Agent, or Firm* — FOX ROTHSCHILD LLP

(57) ABSTRACT

A corpectomy implant device having a solid portion, structural volume and porous end plates configured is disclosed. In some embodiments, the corpectomy device comprises a stochastic lattice structure in the structural volume of the device to reduce stiffness and improve radiolucency. In some embodiments, the porous endplates comprise a lattice configured to provide porosity for bone ingrowth. In some embodiments, endplates are configured to facilitate insertion of the implant between the adjacent vertebrae and to provide anchoring of the corpectomy device to and prevent migration of the device implant in an installed state.

20 Claims, 15 Drawing Sheets

3D PRINTED METAL CORPECTOMY DEVICE WITH STRUCTURAL AND ENDPLATE LATTICE STRUCTURES

CROSS-REFERENCE TO RELATED APPLICATIONS

The present application claims priority from U.S. Provisional Patent Application Ser. No. 63/668,471 filed on 8 Jul. 2024, the entire contents which is incorporated herein by reference.

FIELD

The present technology is generally related to, for example, to spinal stabilization systems, and more particularly, for example, to a corpectomy or, more particularly a cervical corpectomy implant assembly, or for example an interbody implant device having lattice structures that reduce stiffness and improve radiolucency while promoting bone growth into the surface of the device. Embodiments of the devices and methods are described below with reference to the Figures.

BACKGROUND

It is sometimes necessary to remove one or more vertebrae or a portion of one or more vertebrae from the human spine in response to various pathologies. For example, one or more vertebrae may become damaged as a result of tumor growth. Removal, or excision, of a vertebra, may be referred to as a vertebrectomy. Excision of a generally anterior portion of a vertebra, or vertebral body, may be referred to as a corpectomy. An implant is usually placed between the remaining vertebrae to provide structural support for the spine as a part of a corpectomy or vertebrectomy. The implant inserted between the vertebrae may be designed to facilitate fusion or to provide spinal stability between the remaining vertebrae. A successful procedure may decrease pain, preserve or enhance neurological function, and allow a patient greater mobility without an external orthosis. All or part of more than one vertebra may be damaged and require removal and replacement in some circumstances.

Non-surgical treatments, such as medication, rehabilitation, and exercise can be effective; however, they may fail to relieve the symptoms associated with these disorders. Surgical treatment of these spinal disorders includes fusion, fixation, corpectomy, discectomy, laminectomy, and implantable prosthetics. In procedures such as, for example, corpectomy and discectomy, fusion and fixation treatments may be performed that employ implants to restore the mechanical support function of vertebrae. State-of-the art corpectomy devices are too stiff and can make x-ray assessment after surgery difficult. 3D printing portions of the device as a lattice structure can effectively reduce the device stiffness and improve radiolucency (x-ray effectiveness). Lattice structures can also allow bone to grow through the lattices and into the interior of the device, improving the stability of the implant. This disclosure describes an improved corpectomy, vertebrectomy, hemi-vertebrectomy, or other vertebral implant. In some embodiments, such implants may span multiple vertebral levels.

SUMMARY

This disclosure generally relates to a cervical corpectomy implant, comprising:

a structural volume comprising; an anterior volume comprising a first lattice structure, a posterior volume comprising a second lattice structure, a first side volume comprising a third lattice structure, and a second side volume comprising a fourth lattice structure, an upper endplate volume comprising a fifth lattice structure; and a lower endplate volume comprising a sixth lattice structure; wherein one or more of the first lattice structure, the second lattice structure, the third lattice structure, the fourth lattice structure, the fifth lattice structure, and the sixth lattice structures are stochastic, wherein the anterior volume, the posterior volume, the first side volume, the second side volume, the upper endplate volume, and the lower endplate volume each have an average lattice pore size of about 100 to about 500 microns, wherein the anterior volume, the posterior volume, the first side volume, and the second side volume are arranged to form a hollow cavity extending along an axis between the upper endplate volume and the lower endplate volume, wherein the upper endplate volume comprises a first plurality of anti-migration features extending from upper endplate volume surface, and wherein the lower endplate volume comprises a second plurality of anti-migration features extending from lower endplate volume surface.

In some embodiments, the anterior volume, the posterior volume, the first side volume, the second side volume, the upper endplate volume, and the lower endplate volume each have a porosity from about 30% to about 70%. In some embodiments, the upper endplate volume and the lower endplate volume comprise greater porosity compared to the anterior volume, the posterior volume, the first side volume, and the second side volume.

In some embodiments, the anterior volume, the posterior volume, the first side volume, the second side volume, the upper endplate volume, and the lower endplate volume each have a volume fill % from about 50% to about 99%, based on the total volume space occupied by the first lattice structure, the second lattice structure, the third lattice structure, the fourth lattice structure, the fifth lattice structure, and the sixth lattice structure, respectively. In some embodiments, the anterior volume, the posterior volume, the first side volume, and the second side volume comprise the same volume fill %. In some embodiments, the upper endplate volume and the lower endplate volume comprise the same volume fill %. In some embodiments, the upper endplate volume and the lower endplate volume comprise a lower volume fill % compared to the anterior volume fill %, the posterior volume fill %, the first side volume fill %, and the second side volume fill %.

In some embodiments, the anterior volume, the posterior volume, the first side volume, the second side volume, the upper endplate volume, and the lower endplate volume each have a uniform lattice density. In some embodiments, wherein one or more of the anterior volume, the posterior volume, the first side volume, or the second side volume have a lattice density gradient along a direction extending from the lower endplate volume to the upper endplate volume.

In some embodiments, the first side volume and the second side volume each comprise a plurality of lateral holes. In some embodiments, the anterior volume comprises a threaded hole configured to attach to an insertion instrument and/or one or more graft holes configured for insertion of bone graft materials. In some embodiments, the implant further comprises a solid frame that partially encloses one or more of the anterior volume, the posterior volume, the upper endplate volume, and the lower endplate volume. In some embodiments, the solid frame partially encloses the anterior volume, the posterior volume, the upper endplate volume, and the lower endplate volume. In some embodiments, the solid frame partially encloses the upper endplate volume and the lower endplate volume. In some embodiments, the solid frame partially encloses the upper endplate volume and the lower endplate volume.

In some embodiments, the anti-migration feature is a teeth structure, and wherein the teeth structure comprises a triangular structure with a shallow angle incline configured to facilitate insertion of the cervical corpectomy implant and a steep angle incline configured to suppress migration of the cervical corpectomy implant. In some embodiments, the shallow angle incline ranges from about 5° to about 40° and the steep angle incline ranges from about 50° to about 85°.

In some embodiments, the implant further comprises a first chamfered edge at an intersection of the anterior volume and the upper endplate volume, and a second chamfered edge at an intersection of the anterior volume and the lower endplate volume, wherein the first chamfered edge and the second chamfered edge are each inclined at an angle from about 15° to about 60°.

Another aspect of this disclosure generally relates to a method for treating a plurality of vertebrae regions in a patient, the method comprising: inserting a cervical corpectomy implant between an upper and lower vertebrae, wherein the cervical corpectomy implant comprises: a structural volume comprising; an anterior volume comprising a first lattice structure, a posterior volume comprising a second lattice structure, a first side volume comprising a third lattice structure, and a second side volume comprising a fourth lattice structure, an upper endplate volume comprising a fifth lattice structure; and a lower endplate volume comprising a sixth lattice structure; wherein one or more of the first lattice structure, the second lattice structure, the third lattice structure, the fourth lattice structure, the fifth lattice structure, and the sixth lattice structures are stochastic, wherein the anterior volume, the posterior volume, the first side volume, the second side volume, the upper endplate volume, and the lower endplate volume each have an average lattice pore size of about 100 to about 500 microns, wherein the anterior volume, the posterior volume, the first side volume, and the second side volume are arranged to form a hollow cavity extending along an axis between the upper endplate volume and the lower endplate volume, wherein the upper endplate volume comprises a first plurality of anti-migration features extending from upper endplate volume surface, and wherein the lower endplate volume comprises a second plurality of anti-migration features extending from lower endplate volume surface, attaching the upper endplate volume to the upper vertebrae in a configuration that the first plurality of anti-migration features engages with an inferior surface of the upper vertebrae; positioning the cervical corpectomy implant within a gap between the upper and the lower vertebrae; attaching the lower endplate volume to the lower vertebrae in a configuration that the second plurality of anti-migration features engages with a superior surface of the lower vertebrae; placing a cervical plate adjacent to the anterior volume; inserting a first bone through the cervical plate into the upper vertebrae and inserting a second bone screw through the cervical plate into the lower vertebrae to stabilize the corpectomy implant between the upper vertebrae and the lower vertebrae. In some embodiments, the positioning comprises the cervical corpectomy implant spanning more than one vertebral level.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The following drawings are illustrative of particular embodiments of the present disclosure and therefore do not limit the scope of the present invention. The drawings are not to scale and are intended for use in conjunction with the explanations in the following detailed description.

DETAILED DESCRIPTION

Figure 1:
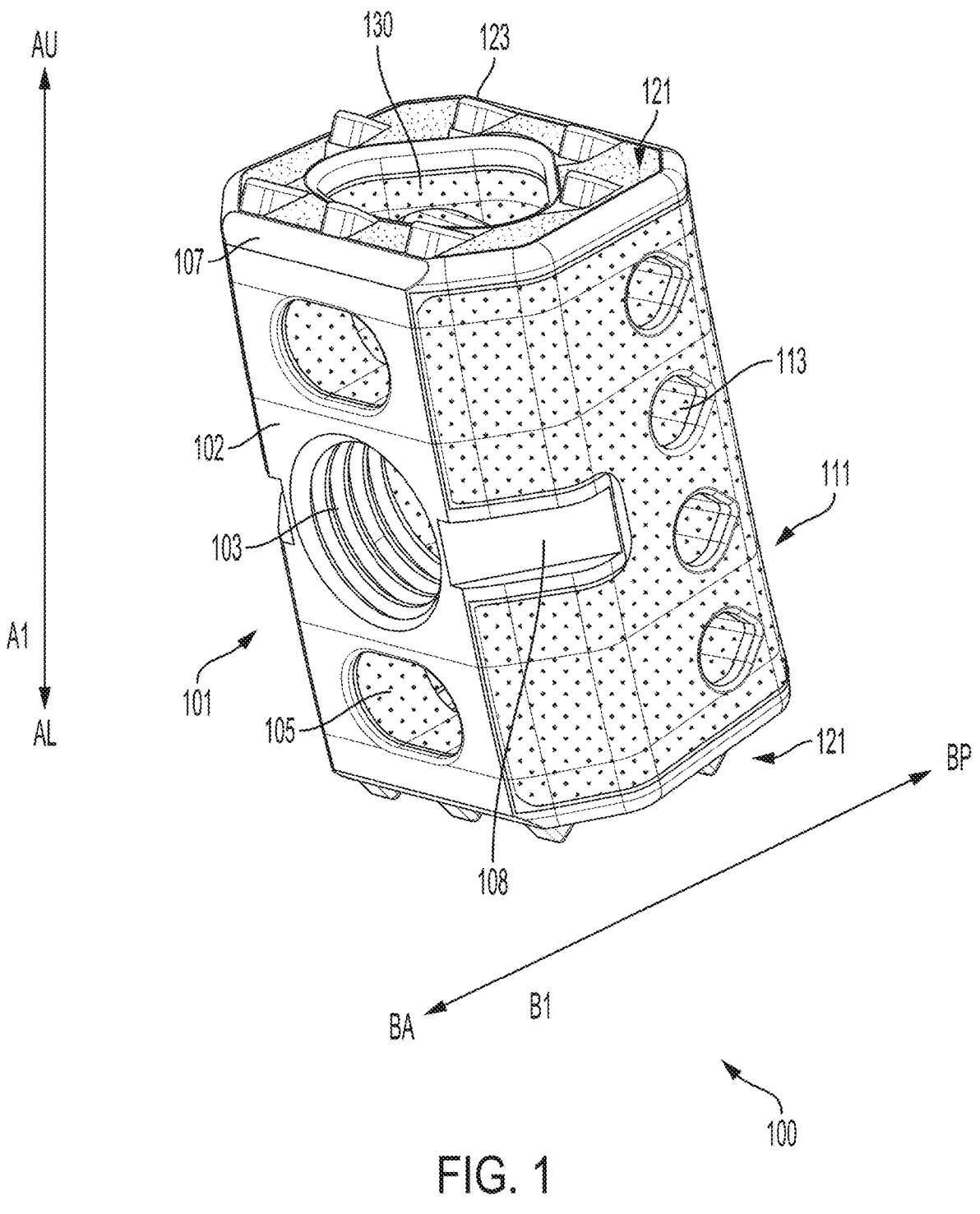
FIG. 1 is a perspective view of a cervical corpectomy implant of the present disclosure.

Embodiments of the present disclosure relate generally, for example, to spinal stabilization systems, and more particularly, to implants used as spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise. Additionally, it shall be understood that the term "about" encompasses a variation of at least +/−10% from the example values and relative characteristics provided herein.

The following discussion includes a description of, for example, a cervical corpectomy implant and related methods of manufacturing the cervical corpectomy implant in accordance with the principles of the present disclosure. Other types of implants are also contemplated, including, for example, intervertebral or corpectomy implants for use in the cervical, thoracic, and lumbar regions of the spine. Alternate embodiments are also disclosed. Reference is made in detail to the exemplary embodiments of the present disclosure, which are illustrated in the accompanying figures. FIGS. 1-16, illustrate various components of a vertebral implant, such as, for example, a cervical corpectomy implant 100, 200, 300, 400, or 500.

Figure 2:
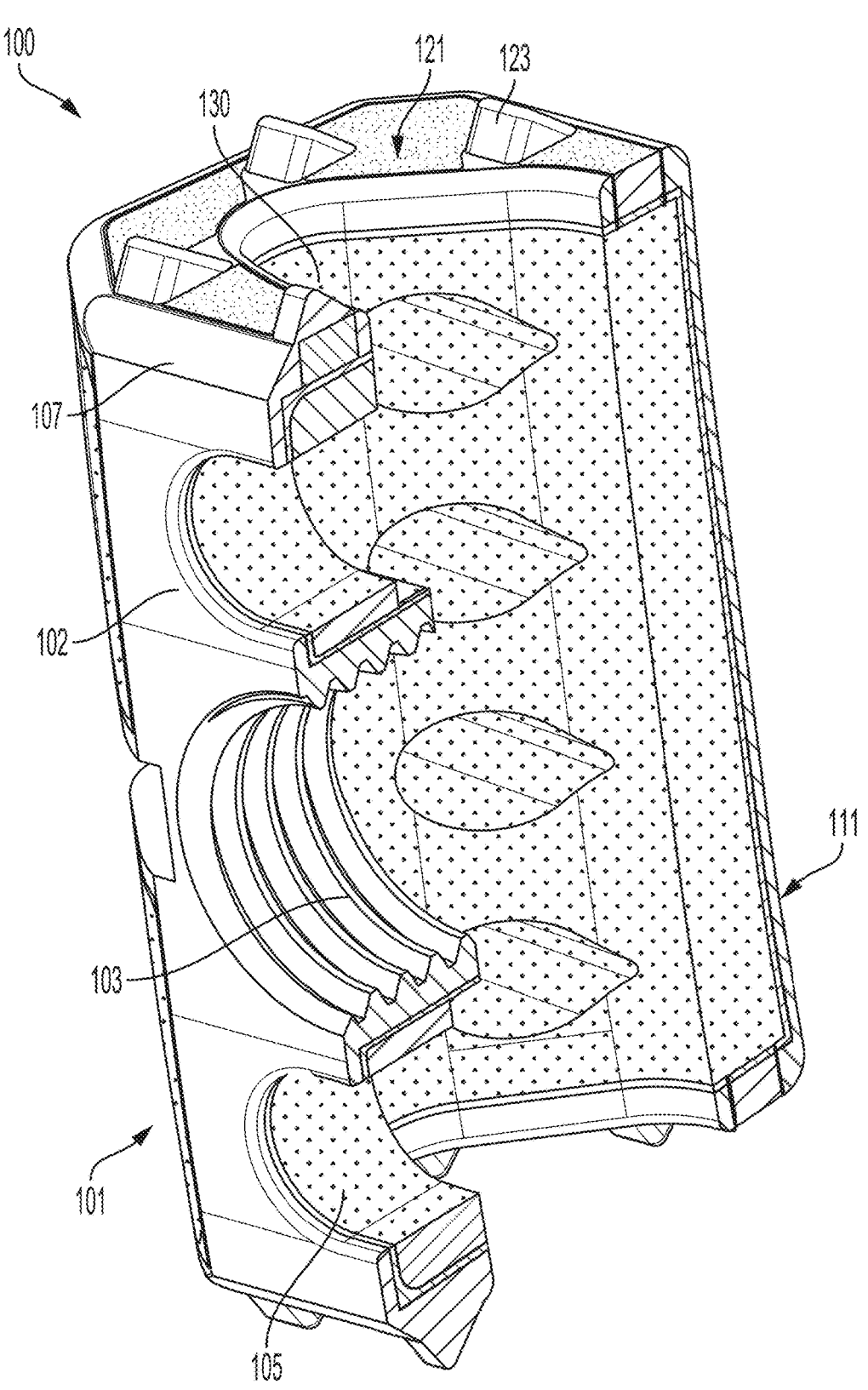
FIG. 2 is a cross-section view of an embodiment of a cervical corpectomy implant.

Referring generally to FIGS. 1 and 2, an embodiment of a cervical corpectomy implant 100 and its cross-section is shown. A cervical corpectomy implant 100 may comprise solid body portion 101 extending substantially parallel lengthwise along longitudinal axis A1 and widthwise along latitudinal axis B1. In some embodiments, solid body portion 101 may comprise structural volume 111, and endplate volume 121. In some embodiments, structural volume 111 may comprise an anterior volume 161 (as seen best in FIG. 4), a posterior volume 162 (as seen best in FIG. 5), two side volumes 163 (as seen best in FIGS. 6 and 7), two endplate volumes 121 (as best seen in FIGS. 1-3 and 8). In some embodiments, structural volume 111 may be extended along longitudinal axis A1 between an upper endplate volume (as indicated AU) and a lower endplate volume (as indicated by AL). In some embodiments, the upper endplate volume and the lower endplate volume are substantially parallel to each other and substantially normal (perpendicular) to structural volume 111.

In some embodiments, cervical corpectomy implant 100 may have a length (extending along A1) from about 10 mm to about 60 mm, about 15 mm to about 55 mm, about 20 mm to about 50 cm, about 25 mm to about 45 mm, about 30 mm to about 40 mm, about 10 mm to about 15 mm, about 15 mm to about 20 mm, about 20 mm to about 25 mm, about 25 mm to about 30 mm, about 30 mm to about 35 mm, about 35 mm to about 40 mm, about 40 mm to about 45 mm, about 45 mm to about 50 mm, about 50 mm to about 55 mm, about 55 mm to about 60 mm, or between any two aforementioned values. In some embodiments, solid body portion 101 may be extended along latitudinal axis B1 comprising an anterior portion (as indicated BA) and a posterior portion (as indicated by BP). In some embodiments, implant 100 may have a width (extending along B1) from about 10 mm to about 20, about 10 mm to about 12 mm, about 12 mm to about 14 mm, about 14 mm to about 16 mm, about 16 mm to about 18 mm, about 18 mm to about 20 mm, or between any two aforementioned values.

In various embodiments, solid body portion 101 may comprise solid frame 102 comprising biologically acceptable materials suitable for medical applications, including metals, synthetic polymers, ceramics, and bone material and/or their composites. In various embodiments, the components, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of cPEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyketide, polyglycolide, polytyrosine carbonate, polycaprolactone, polylactic acid or polylactide and their combinations.

In some embodiments, structural volume 111 serves as the primary structural volume for the device providing rigidity and/or flexibility when installed in a patient. In some embodiments, structural volume 111 may have a uniform lattice or porosity along both A1 and B1 axes. As used herein, the term "lattice" refers to a repeating, grid-like pattern or matrix of interconnected elements within a 3D object that fill a volume or conform to a surface. Interconnected elements may include but are not limited to beams, surfaces, or plates interconnected to form a 3D framework. Lattice structures described in this document may be an ordered structure like a honeycomb or exhibit partial or full random, stochastic structures.

As used herein, the term "stochastic structure" refers to a type of lattice structure where the arrangement of points and connecting beams is not based on a regular pattern, but rather on a random distribution within a defined volume. This random arrangement creates a non-uniform, open-cell structure provide greater flexibility of the lattice structure without sacrificing structural integrity of the lattice structure. Moreover, non-uniform lattice structure allows for more optimized bone growth throughout the random lattice structure providing greater stability of the boney growth structure.

In some embodiments, structural volume 111 may have a lattice or porosity gradient along one or both A1 and B1 axes. For instance, implant 100 may have a lower degree of porosity (i.e., higher degree of volume fill) at the lower portion of implant, e.g., AL, and may have a higher degree of porosity (i.e., lower degree of volume fill) at higher portion of implant, e.g., AU. In some embodiments, looser lattice structure (higher porosity) structures reduce the stiffness and radio-opacity (improve radiolucency) of the device.

In some embodiments, average pore size of structural volume 111 may range from about 100 microns to about 500 microns, about 100 microns to about 150 microns, about 100 microns to about 150 microns, about 150 microns to about 200 microns, about 200 microns to about 250 microns, about 250 microns to about 300 microns, about 300 microns to about 350 microns, about 350 microns to about 400 microns, about 400 microns to about 450 microns, about 450 microns to about 500 microns, or between any two aforementioned values.

In some embodiments, endplate volume 121 serves as the primary interface that promotes boney ingrowth. In some embodiments, porosity of endplate volume 121 may be achieved by lattice structure similar that found in structural volume 111 or may be a perforated solid material such as but not limited to stainless steel alloys, titanium alloys, or cobalt-chrome alloys. In some embodiments, average pore size of endplate volume 121 may range from about 100 microns to about 500 microns, about 100 microns to about 150 microns, about 100 microns to about 150 microns, about 150 microns to about 200 microns, about 200 microns to about 250 microns, about 250 microns to about 300 microns, about 300 microns to about 350 microns, about 350 microns to about 400 microns, about 400 microns to about 450 microns, about 450 microns to about 500 microns, or between any two aforementioned values.

Figure 3:
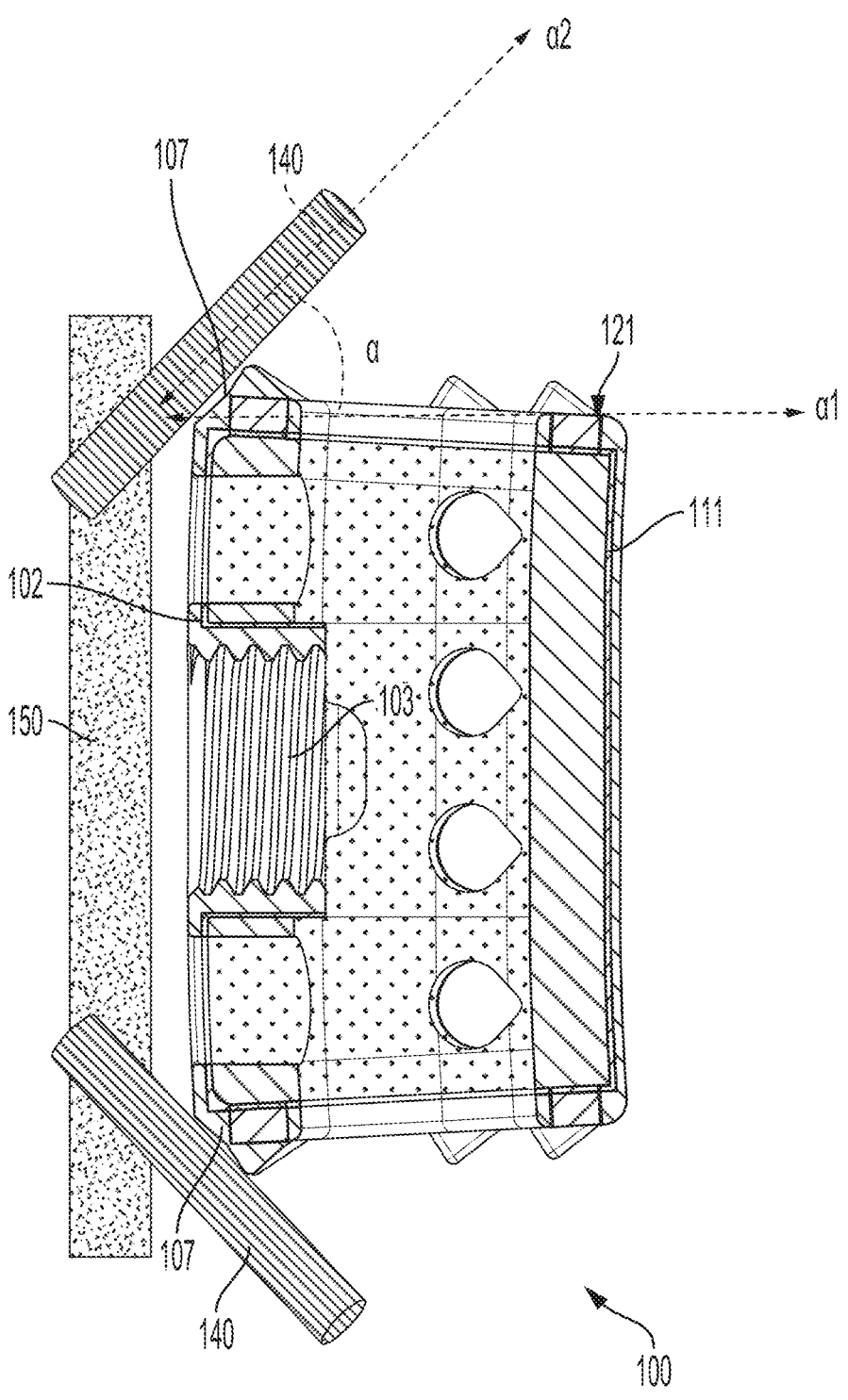
FIG. 3 is a side cross-section view of an embodiment of a cervical corpectomy implant.

In some embodiments, as better seen in FIGS. 2 and 3, solid frame 102 may be configured to encompass, or encapsulate structural volume 111. In some embodiments, as seen in FIGS. 1 and 3, solid frame 102 may partially enclose the anterior portion or side BA, posterior portion or side BP, two side portions, and upper and lower endplate volume (AL and AU, respectively), i.e., endplate volume 121 of implant 100. In some embodiments, solid frame 102 may be monolithic structure or may be a connection of various modular components, e.g., a frame enclosing the perimeter of upper and lower endplate volumes 121, a first solid plate positioned at anterior side (BA) of structural volume 111 (i.e., solid body portion 101), a second solid plate positioned at posterior side (BP) of structural volume 111.

Many embodiments are principally directed to 3D printing technologies and other additive manufacturing processes. However, in some embodiments, subtractive manufacturing processes may also be applied to portions and sub-features of the disclosed implants. Various embodiments and components may be manufactured by a subtractive manufacturing process including, but not limited to, machining (e.g., machining tools, such as saws, lathes, milling, machines, drill presses, electrical discharge machining (EDM)) is used to physically remove material to achieve the desired geometry and dimensions of the lattices and pores structures. In some embodiments, surface treatment steps may be applied to provide porous structures on the implant.

In some embodiments, solid body portion 101 may comprise a threaded hole 103 configured to provide an attachment mechanism for an insertion instrument. In some embodiments threaded hole 103 may be configured to receive bone graft material that may be injected through threaded hole 103 and into a hollow, interior cavity or graft chamber 130 of cervical corpectomy implant 100. In some embodiments, threaded hole 103 may be circular and have a diameter from about 2 mm to about 6 mm, about 2 mm to about 4 mm, about 4 mm to about 6 mm, about 2 mm, about 3 mm, about 4 mm, about 5 mm, about 6 mm, or between any two aforementioned values. In some embodiments, implant 100 may comprise engagement slot 108 for an attachment of insertion instrument for installation of implant 100 to patient.

In the illustrated embodiment, graft chamber 130 extends lengthwise along longitudinal axis A1 providing a lengthwise cavity through implant 100. In some embodiments, interior cavity or graft chamber 130 may be configured to allow for bone graft material to be packed within the device. In some embodiments, solid body portion 101 may comprise one or more graft hole(s) 105 configured to accept osteogenic material, bone graft, or other bone growth and healing substances to facilitate bone growth and/or improve radiolucency of the device. In some embodiments, graft hole 105 may generally comprise circular, oval, or polygonal shape openings, including, for example, generally triangular, diamond, square, rectangular, or hexagonal shapes. In some embodiments, when graft hole 105 is circular or oval, graft hole 105 may have a diameter (or the longest distance between two points outer perimeter graft hole 105 is non-circular) of about 5 mm to about 15 mm, about 5 mm to about 7 mm, about 7 mm to about 9 mm, about 9 mm to about 11 mm, about 11 mm to about 13 mm, about 13 mm to about 15 mm, or between any two aforementioned values As seen in FIGS. 1-3, in some embodiments, cervical corpectomy implant 100 may comprise a sloped or chamfered edge 107 at the edge intersection of anterior volume and upper endplate volume 121 and edge intersection of anterior volume lower endplate. In some embodiments, chamfered edge 107 provide a sloped surface for one or more cervical plate bone screws 140 to be placed adjacent to the device and allow stabilizing cervical plate 150 to be placed adjacent to the implant. Chamfered edge may provide enough clearance such that bone screw 140 does not come in contact with cervical corpectomy implant 100 or a. In some embodiments, chamfered edge 107 may be inclined at an angle $\alpha$ (as seen in FIG. 3), measured between upper plane $\alpha 1$ of implant 100 and bone screw trajectory $\alpha 2$. In some embodiments, angle $\alpha$ may range from about 15° to about 60°, about 20° to about 55°, about 25° to about 50°, about 30° to about 45°, about 35° to about 40°, about 15° to about 20°, about 20° to about 25°, about 25° to about 30°, about 30° to about 35°, about 35° to about 40°, about 40° to about 45°, about 45° to about 50°, about 50° to about 55°, about 55° to about 30°, or between any two aforementioned values, based on the position of the bone screw trajectory $\alpha 2$.

In some embodiments, cervical corpectomy implant 100 may comprise structural volume 111 comprising more open lattice structures configured to reduce the stiffness and radio-opacity of the implant. In some embodiments, structural volume 111 may comprise a plurality of lateral holes 113 configured for facilitating fusion between the graft chamber and adjacent bone for bone graft packing and/or to further improve radiolucency. In some embodiments, implant 100 may comprise from 1 to 5 lateral hole(s) 113 depending on the length of implant 100.

Referring now to FIGS. 4-8, various perspectives of a cervical corpectomy implant 100 showing lattice structures in structural volume 111 are shown. In various embodiments, the cervical corpectomy implant disclosed in FIGS. 4-8 may have the same, similar and/or substantially the same features and functionality as explained above with respect to cervical corpectomy implant in FIGS. 1-3.

Figure 5:
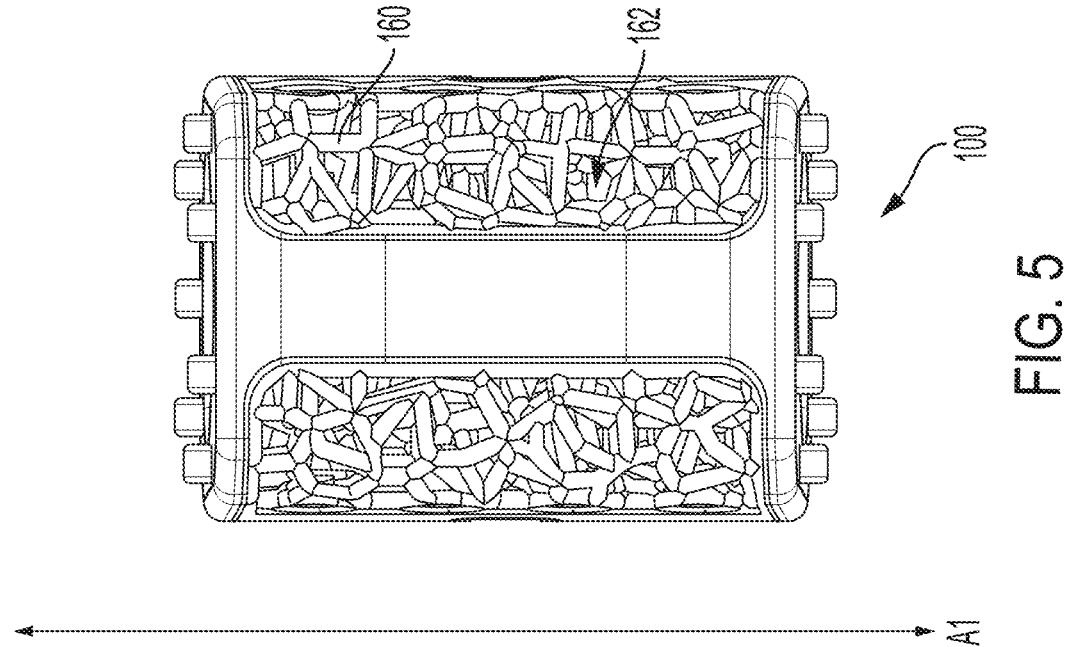
FIG. 5 is a rear perspective view of an embodiment of a cervical corpectomy implant.
Figure 4:
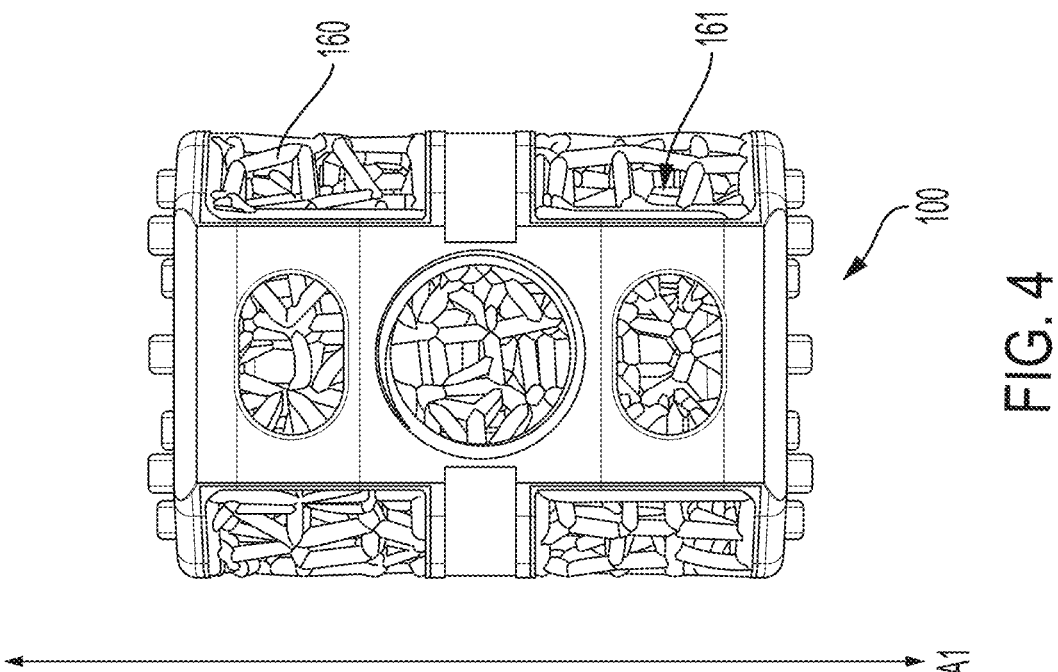
FIG. 4 is a front perspective view of an embodiment of a cervical corpectomy implant.
Figures 6, 7:
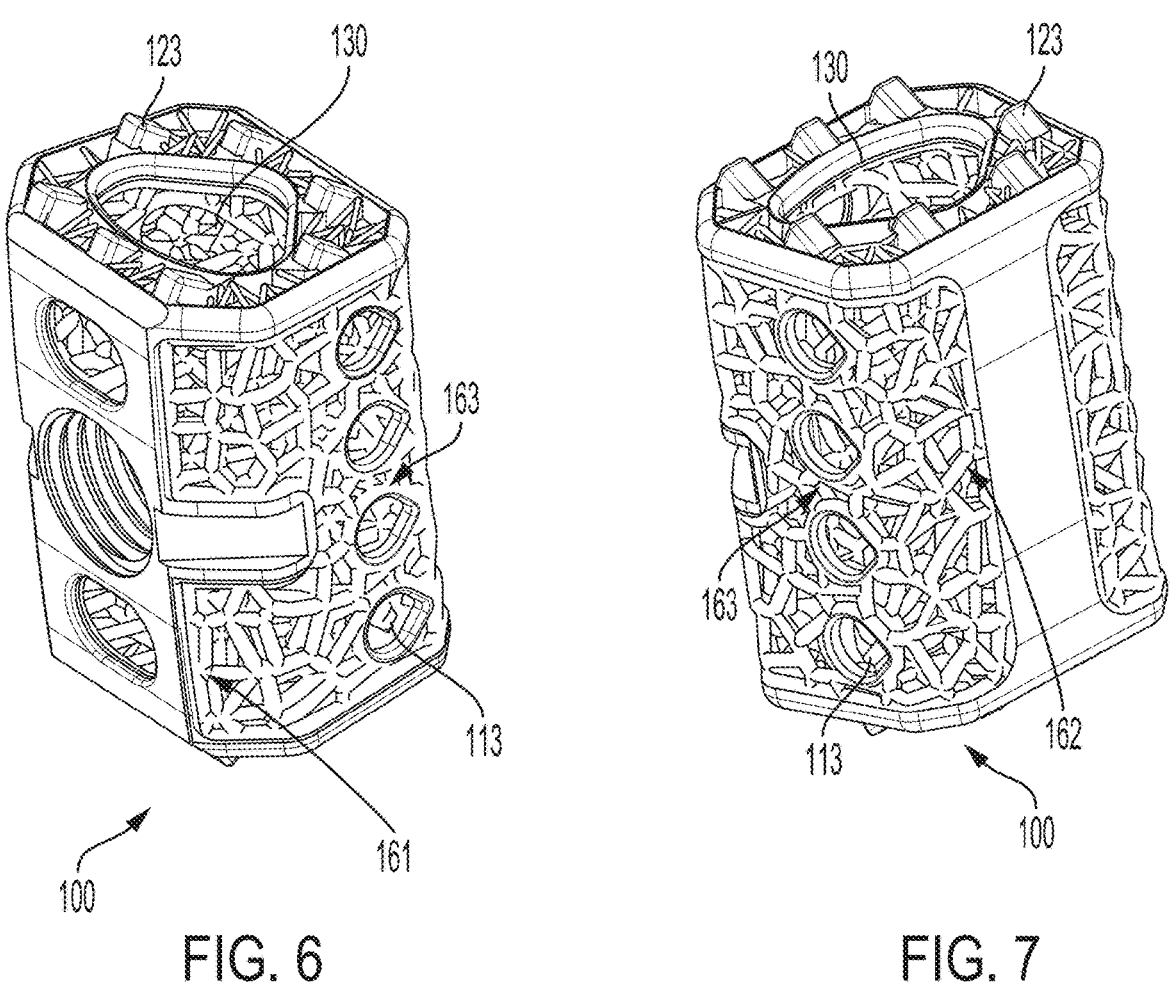
FIG. 6 is a perspective view of an embodiment of a cervical corpectomy implant.
FIG. 7 is another perspective view of an embodiment of a cervical corpectomy implant.

FIGS. 4 and 5 show anterior volume 161 and posterior volume 162 of structural volume 111. FIGS. 6 and 7 show perspective views of side volumes 163 of structural volume 111. As seen in FIGS. 4-7, structural volume 111 may comprise stochastic, or random, lattice structures 160 filling the volume space of structural volume 111. As used herein, the term "lattice" refers to a repeating, grid-like pattern or matrix of interconnected elements within a 3D object that fill a volume or conform to a surface. Interconnected elements may include but are not limited to beams, surfaces, or plates interconnected to form a 3D framework. Lattice structures described in this document may be an ordered structure like a honeycomb or exhibit partial or full random, stochastic structures.

In some embodiments, lattice structures 160 may comprise a periodic or repeating lattice structure of one or more shapes including but not limited to squares, rectangles, diamonds, or other higher-dimension polygonal structures such as pentagons, hexagons, or octagons. In some embodiments, any part (e.g., anterior volume, e.g., 161; posterior volume, e.g., 162; side volume, e.g., 163; or endplate volume, e.g., 121) of structural volume 111 comprising the lattice structure 160 may each have a volume fill from about 50% to about 99%, about 50% to about 95%, about 55% to about 90%, about 60% to about 85%, about 65% to about 80% about 70% to about 75%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, about 95% to about 99%, or between any two aforementioned values, of the volume space of structural volume 111 (or anterior volume, e.g., 161; posterior volume, e.g., 162; side volume, e.g., 163; or endplate volume, e.g., 121). As used herein, "average volume fill percentage," "volume fill percentage," or "volume fill %" refers to the percentage of lattice that occupies the void space within the total volume of the structure. For instance, 50% volume fill percentage in a side wall volume indicates that half of the volume is occupied by the lattice and 50% is empty or open space.

In some embodiments, anterior volume 161, posterior volume 162, and two side volumes 163 may comprise the same volume fill %. In some embodiments, upper endplate volume and lower endplate volume may comprise the same volume fill %. In some embodiments, upper endplate volume and the lower endplate volume each may comprise lower volume fill % compared to anterior volume 161, posterior volume 162, and two side volumes 163, and the second side volume.

As used herein, the term "porosity" refers to the percentage of volume space in a that is occupied by pores, void spaces, or openings within the lattice structure. In some embodiments, porosity refers to the areas where the solid material is absent that made within the total volume of the structure. In some embodiments, pores may vary in size, shape, and distribution, impacting the overall structure or stochasticity of the lattice.

In some embodiments, any component (any one of anterior volume, e.g., 161; posterior volume, e.g., 162; side volume, e.g., 163; or endplate volume, e.g., 121) of structural volume 111 comprising the lattice structure 160 may have a porosity from about 30% to about 70%, about 30% to about 35%, about 35% to about 40%, about 40% to about 45%, about 45% to about 50%, about 50% to about 55%, about 55% to about 60%, about 60% to about 65%, about 65% to about 70%, about 30% to about 65%, about 35% to about 60%, about 40% to about 55%, about 45% to about 55%, or between any two aforementioned values, of the volume space of structural volume 111 (independently anterior volume, e.g., 161; posterior volume, e.g., 162; side volume, e.g., 163; or endplate volume, e.g., 121).

In some embodiments, any one or more of structural volume 111 component (anterior volume, posterior volume, side volume, or endplate volume) may the same the same porosity or different porosity. In some embodiments, the upper endplate volume and the lower endplate volume may comprise greater porosity compared to anterior volume 161, posterior volume 162, and two side volumes 163. In some embodiments, anterior volume 161 and posterior volume 162 may have lower porosity compared to two side volumes 163. This configuration allows anterior volume 161 and posterior volume 162 to have a tighter lattice structure that does not allow bone to grow to the outside of device.

As used herein, the term "lattice density" refers to the degree of "tightness" of lattice structure in a given structural volume or the distribution of volume fill % throughout a given structural volume. For example, an exemplary side volume having an average of 80% volume fill, (80% of volume space is occupied by lattice structure) may have a uniform lattice density, i.e., degree of tightness is uniform throughout the volume. In this configuration the any given subsection or a portion of the structural volume will comprise the same or similar volume fill %. In another example, a structural volume having a lattice density gradient will have different volume fill % at different parts throughout the volume space. For example, a side volume (e.g., 163) having an overall or average volume fill of 80% may have higher volume fill %, i.e., 90% fill throughout the first half of the volume space in a given direction within the volume space, and have lower fill %, i.e., 70% fill throughout the remaining half of the volume space providing an average of 80% volume fill.

In some embodiments, lattice density may be uniform in a plane or cross-section along longitudinal axis A1 (see FIG. 1). In other words, given any planar cross-section of structural volume 111 along longitudinal axis A1, there is no gradient in lattice density from the bottom of the cross-section to the top of the cross-section. In some embodiments, lattice density may be uniform in a plane or cross-section along latitudinal axis B1 (see FIG. 1). In other words, given any planar cross-section of structural volume 111 along longitudinal axis B1, there is no gradient in lattice density between two side walls.

In some embodiments, lattice density may have a gradient or density in a plane or cross-section along longitudinal axis A1 (see FIG. 1). For instance, given any planar cross-section of structural volume 111 along longitudinal axis A1, the lattice density may increase, decrease, or fluctuate extending from the bottom of the cross-section to the top of the cross-section. Likewise, in some embodiments, lattice density may be uniform in a plane or cross-section along latitudinal axis B1 (see FIG. 1). For instance, given any planar cross-section of structural volume 111 along latitudinal axis B1, the lattice density may increase, decrease, or fluctuate extending between two side walls of implant 100.

The capability for any given structural volume to have varying lattice fill %, porosity, stochasticity, and lattice density allows for the disclosed corpectomy device to be tailored to fit into specific surgical areas where certain portions of the corpectomy implant may need to be stiffer to provide structural rigidity to a certain portion of the implant (by having higher lattice density and/or porosity), or may need to be less stiff to provide sufficient porosity for boney growth outside or around the device to be achieved (by having lower lattice density), all while providing an overall structural stability of the implant and maintaining higher radiolucency compared to solid metal implants.

Figure 8:
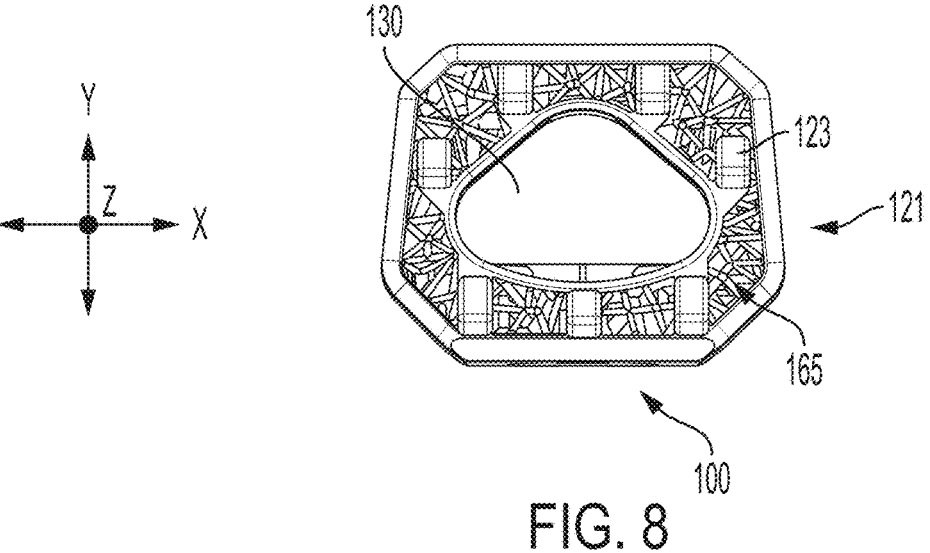
FIG. 8 is a top-down view of an embodiment of a cervical corpectomy implant.

Now referring to FIG. 8, a top-down perspective view of cervical corpectomy implant 100 is shown. As seen in FIG. 8, cervical corpectomy implant 100 may include endplate volume 121 that comprises endplate lattice 165 that includes a different lattice density as compared to the density of anterior volume 161, posterior volume 162, and side volume 163 of structural volume 111. In some embodiments, endplate lattice 165 may fill from about 50% to about 99%, about 50% to about 95%, about 55% to about 90%, about 60% to about 85%, about 65% to about 80% about 70% to about 75%, about 50% to about 55%, about 55% to about 60%, about 60% to about 65%, about 65% to about 70%, about 70% to about 75%, about 75% to about 80%, about 80% to about 85%, about 85% to about 90%, about 90% to about 95%, about 95% to about 99%, or between any two aforementioned values, of the volume space of endplate volume 121.

In some embodiments, endplate volume 121 may comprise a perforated solid material having a porosity that promotes bone ingrowth In some embodiments, average pore size of endplate volume 121 may range from about 100 microns to about 500 microns, about 100 microns to about 150 microns, about 100 microns to about 150 microns, about 150 microns to about 200 microns, about 200 microns to about 250 microns, about 250 microns to about 300 microns, about 300 microns to about 350 microns, about 350 microns to about 400 microns, about 400 microns to about 450 microns, about 450 microns to about 500 microns, or between any two aforementioned values.

Figure 9:
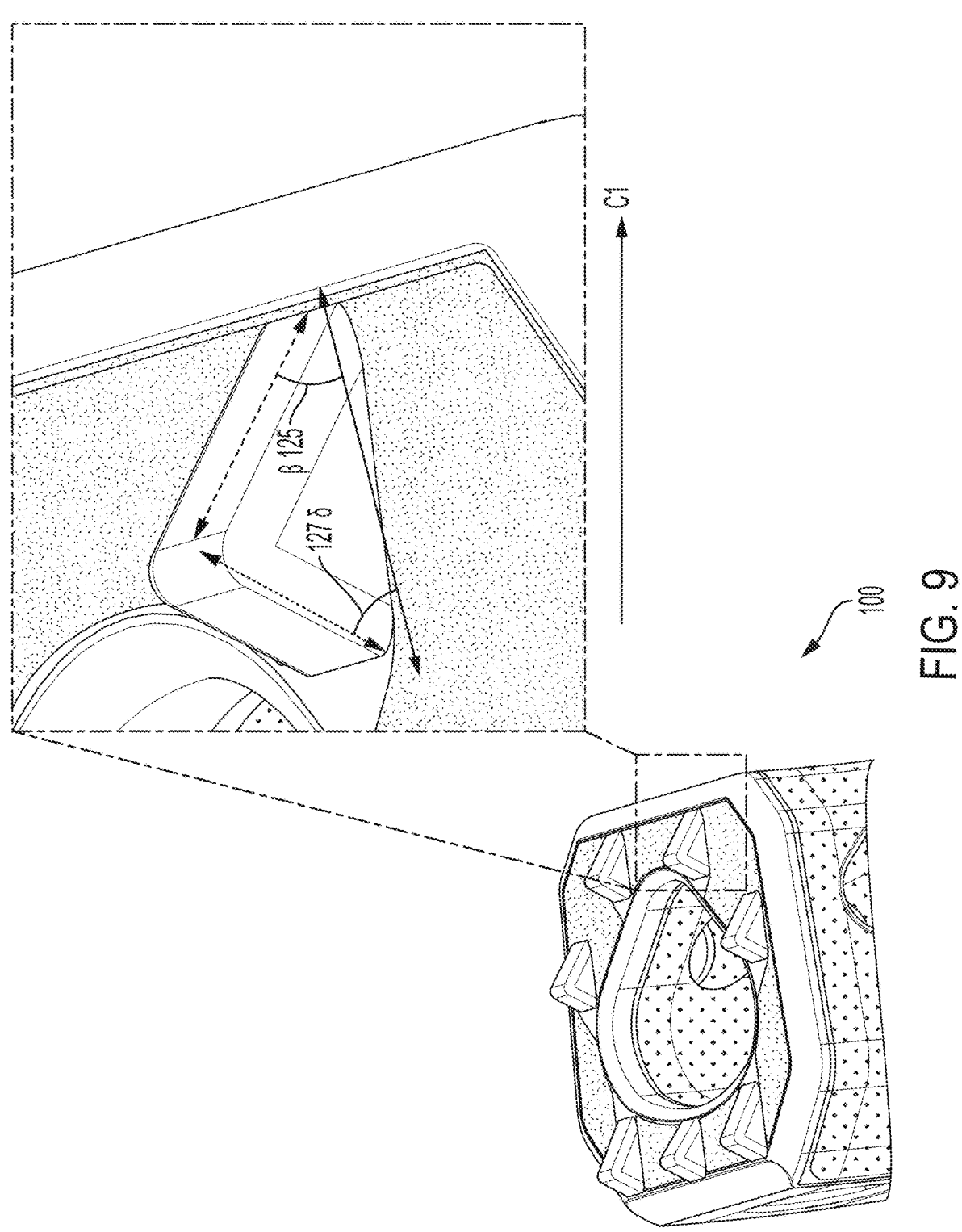
FIG. 9 is a perspective view including an enlarged area of an embodiment of an anti-migration feature of the present disclosure.

In some embodiments, endplate volume 121 may comprise a plurality of anti-migration features such as teeth 123 that engage with the bottom (or top) surface of the superior (or inferior) vertebrae to prevent migration of cervical corpectomy implant 100 from an installed state. In some embodiments, cervical corpectomy implant 100 may comprise 3 to 8, or 3, 4, 5, 6, 7, or 8 anti-migration feature, e.g., teeth 123. In some embodiments as seen in FIG. 9, implant may be inserted into space between vertebra along C1 direction such that shallow angle incline 125 of teeth 123 facilitates the insertion of the implant and steep angle incline 127 reduces/prevents retropulsion, or migration after the implant is inserted.

In some embodiments, the shallow angle incline 125 (angle β) may range from about 5° to about 40°, about 10° to about 35°, about 15° to about 20°, or about 5°, about 10°, about 15°, about 20°, about 25°, about 30°, about 35°, about 40°, or between any two aforementioned values. In some embodiments, steep angle incline 127 (angle δ) may range from about 50° to about 85°, about 55° to about 80°, about 60° to about 75°, about 65° to about 70°, or about 50°, about 55°, about 60°, about 65°, about 70°, about 75°, about 80°, about 85°, or between any two aforementioned values.

Figure 10:
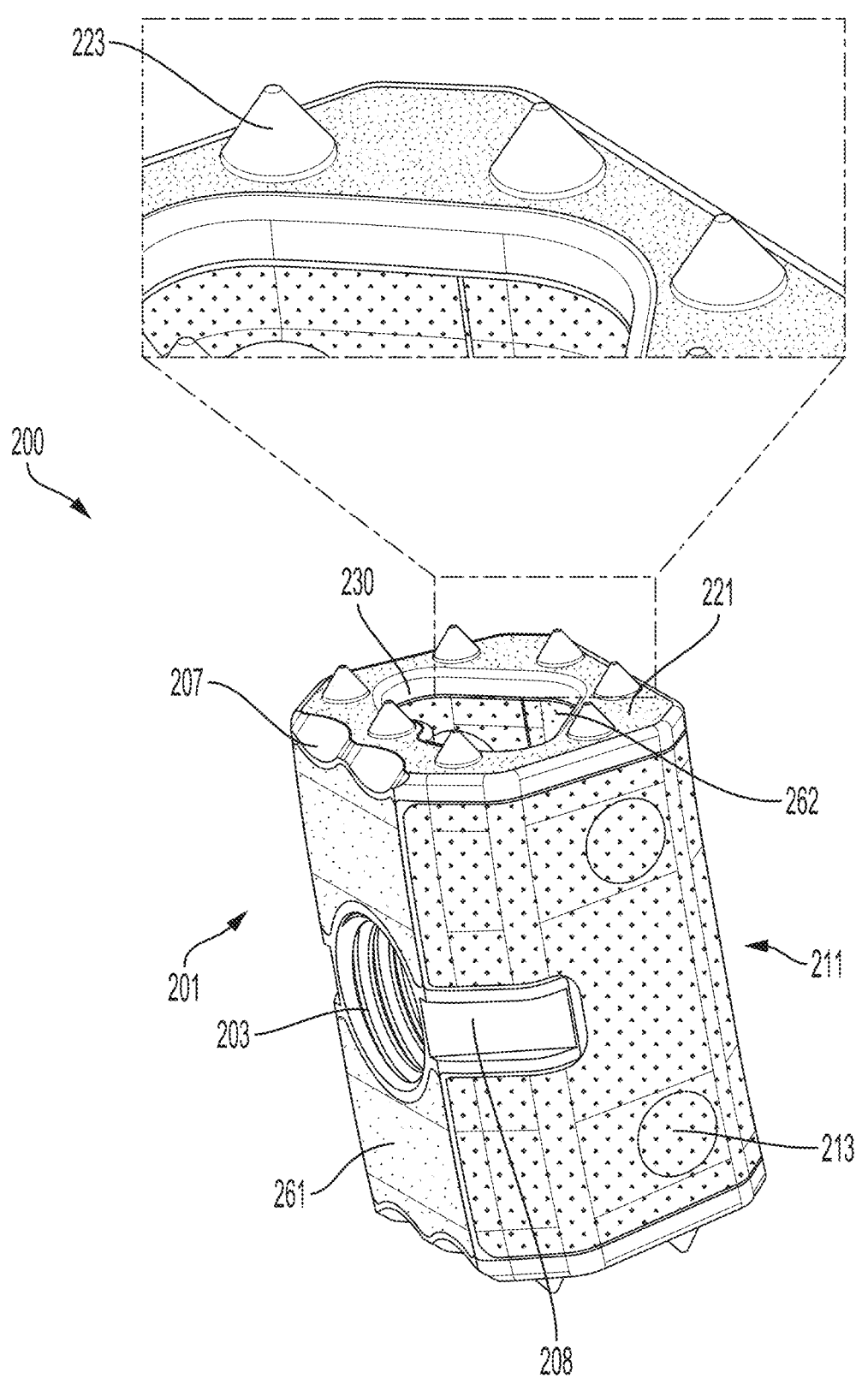
FIG. 10 is a perspective view including an enlarged area of an embodiment of an anti-migration feature of a second embodiment of a cervical corpectomy implant of the present disclosure.
Figure 11:
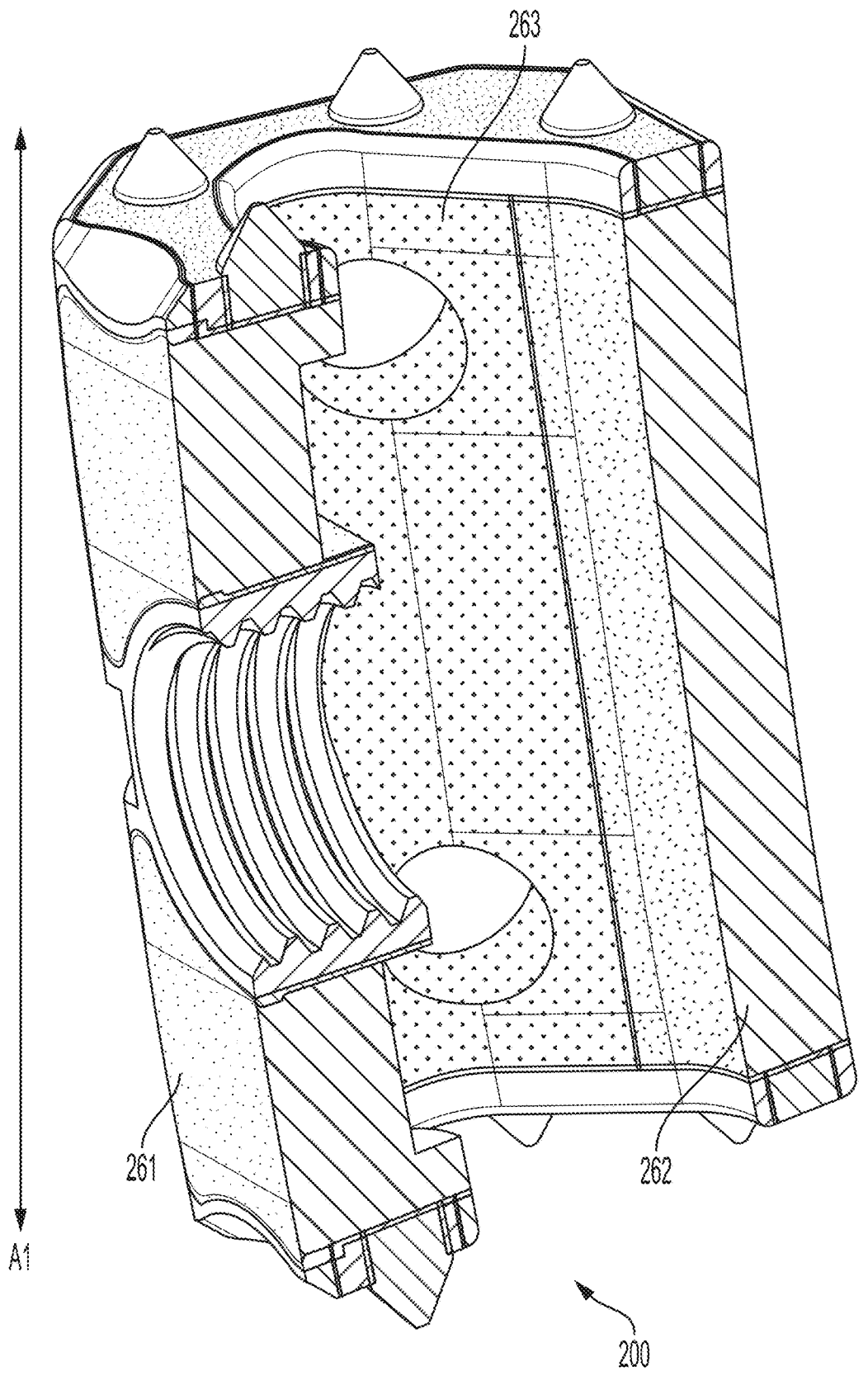
FIG. 11 is a cross-section view of the second embodiment of a cervical corpectomy implant.

Now referring to FIG. 10, a perspective view of a second example of a cervical corpectomy implant 200, is disclosed. In various embodiments, the cervical corpectomy implant 200 as disclosed in FIG. 10 may have the same, similar and/or substantially the same features and functionality as explained above with respect to cervical corpectomy implant 100 in FIGS. 1-8. In various embodiments, cervical corpectomy implant 200 may have the same, similar and/or substantially the same features and functionality as explained above with respect to cervical corpectomy implant 100. For example, cervical corpectomy implant 200 may include, but is not limited to, features such as solid body portion 201, chamfered edge 207, engagement slot 208, structural volume 211, endplate volume 221, threaded hole 203 may be and graft chamber 230 comprising the same, similar and/or substantially the same features. In some embodiments, cervical corpectomy implant 200 may comprise one or more lateral holes 213 on side of structural volume 211 similar to as seen in cervical corpectomy implant 100. In some embodiments, cervical corpectomy implant 200 may comprise one or more graft holes (not shown) on the anterior side of solid body portion 201 that are configured to accept osteogenic material, bone graft, or other bone growth and healing substances to facilitate bone growth and/or improve radiolucency of the device. In some embodiments, cervical corpectomy implant 200 may not include a solid frame (e.g., solid frame 102) that encompasses, or encapsulates structural volume 211, Instead, as seen in FIGS. 10 and 11, cervical corpectomy implant 200 may comprise anterior volume 261 and posterior volume 262. Compared to solid frame 102, anterior volume 261 and posterior volume 262 may provide additional reduction in stiffness improving flexibility, and improve radiolucency.

As seen further in FIG. 10, cervical corpectomy implant 200 may comprise anti-migration features on endplate volume 221, e.g., conical spike(s) 223, to prevent migration of cervical corpectomy implant 200 from an installed state. In some embodiments, cervical corpectomy implant 200 may comprise 3 to 8, or 3, 4, 5, 6, 7, or 8 anti-migration feature 123 In some embodiments, any anti-migration feature disclosed in the present disclosure may be used with any cervical corpectomy implant disclosed in this document.

As seen in FIG. 11, in some embodiments, lattice density or degree of randomness (stochastic property) may be different between anterior volume 261, posterior volume 262, and side volume 263 to control or modulate bone ingrowth/graft packing to certain directions. In some embodiments, anterior volume 261 and posterior volume 262 may have a tight lattice structure that does not allow bone to grow to the outside of the device along the anterior and the posterior directions. In some embodiments, lattice structures of anterior volume 261 and posterior volume 262 may independently fill from about 70% to about 99%, about 70% to about 75%, about 75% to about 80%, about 80% to about 85%, about 85% to about 90%, about 90% to about 95%, about 95% to about 99%, or between any two aforementioned values, of the volume space of anterior volume 261 and posterior volume 262.

In some embodiments, average pore size of anterior volume 261 and posterior volume 262 may independently range from about 100 microns to about 500 microns, about 100 microns to about 150 microns, about 100 microns to about 150 microns, about 150 microns to about 200 microns, about 200 microns to about 250 microns, about 250 microns to about 300 microns, about 300 microns to about 350 microns, about 350 microns to about 400 microns, about 400 microns to about 450 microns, about 450 microns to about 500 microns, or between any two aforementioned values. In some embodiments, porosity of anterior volume 261 and posterior volume 262 may independently range from about 70% to about 99%, about 70% to about 75%, about 75% to about 80%, about 80% to about 85%, about 85% to about 90%, about 90% to about 95%, about 95% to about 99%, or between any two aforementioned values, of the volume space of anterior volume 261 and posterior volume 262.

Figure 12:
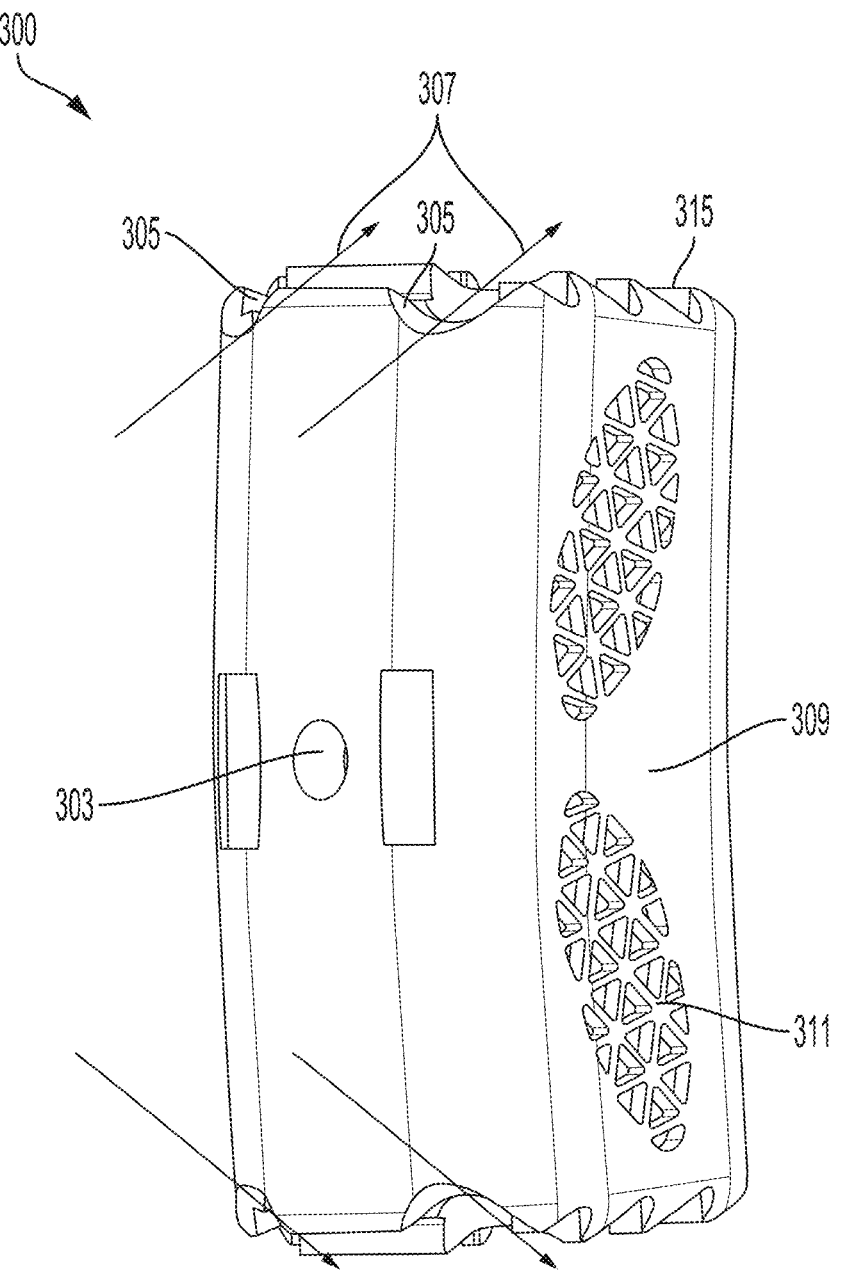
FIG. 12 is a perspective view of a third embodiment of a cervical corpectomy implant of the present disclosure.
Figure 13:
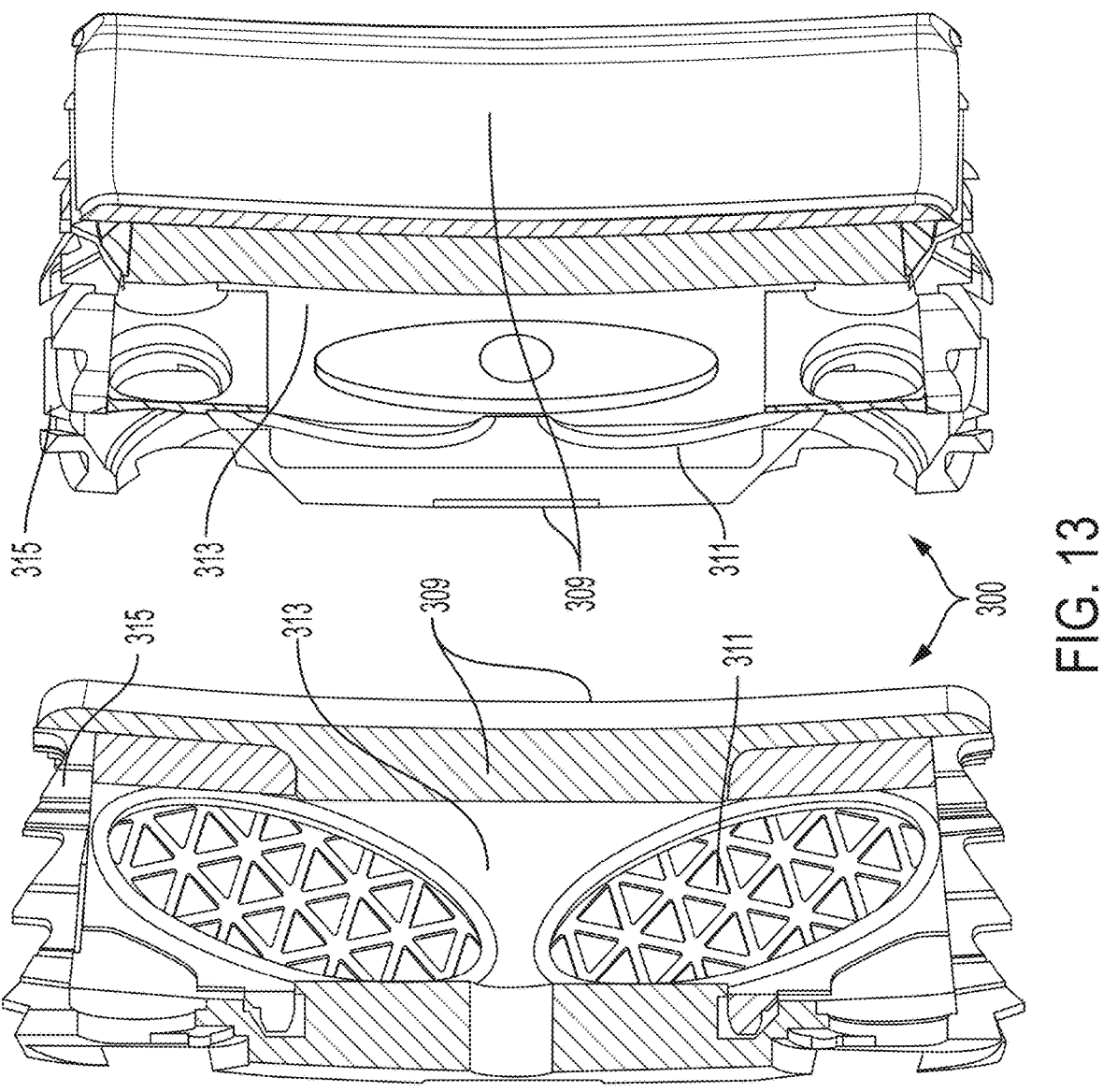
FIG. 13 is an exploded parts view of the third example of a cervical corpectomy implant.

Now referring to FIG. 12, a perspective view of a third example of a cervical corpectomy implant 300, is disclosed. In various embodiments, cervical corpectomy implant 300 may have the same, similar and/or substantially the same features and functionality as explained above with respect to cervical corpectomy implant 100 or 200 such as threaded hole 303 that may be configured to provide an attachment mechanism for an insertion instrument. As seen in FIG. 12, cervical corpectomy implant 300 may comprise one or more grooves 305 that is configured to provide clearance for cervical bone screw trajectory 307. Such grooves 305 may be indents or relief areas such that the cervical bone screw does not make contact with grooves 305. In other embodiments, such indents or relief areas of grooves 305 may make contact with the cervical bone screw. As seen in FIG. 12 and the exploded view in FIG. 13, cervical corpectomy implant 300 may comprise outer shell 309 enclosing the interior implant lattice. In some embodiments, cervical corpectomy implant 300 may comprise sagittal window frame 311 to provide bone ingrowth and injection of bone graft materials. In some embodiments, sagittal window frame 311 may comprise circular shape openings and/or various polygonal shape openings, including, for example, triangular, diamond, square, rectangular, or hexagonal shapes. In some embodiments, the interior of cervical corpectomy implant 300 may comprise core lattice 313 which is configured to provide bone ingrowth and reduce stiffness and radiolucency. In some embodiments, cervical corpectomy implant 300 may comprise end cap lattice 315 comprises different lattice density and/or stochastic properties compared to core lattice 313. In some embodiments, outer shell 309 may be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO₄ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of cPEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyketide, polyglycolide, polytyrosine carbonate, polycaprolactone, polylactic acid or polylactide and their combinations.

Figure 14B:
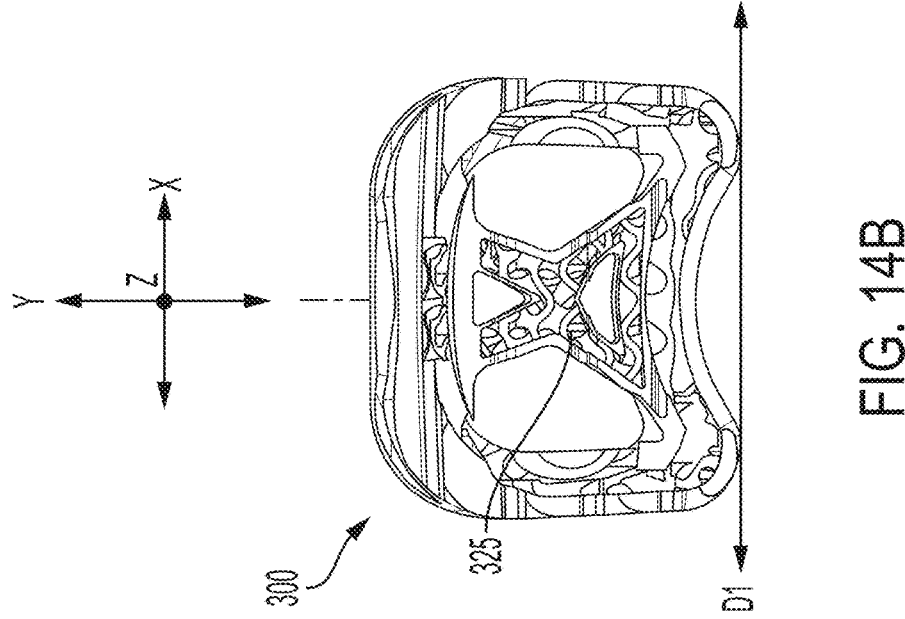
FIG. 14B is a top-down perspective view of the third example of a cervical corpectomy implant.
Figure 14A:
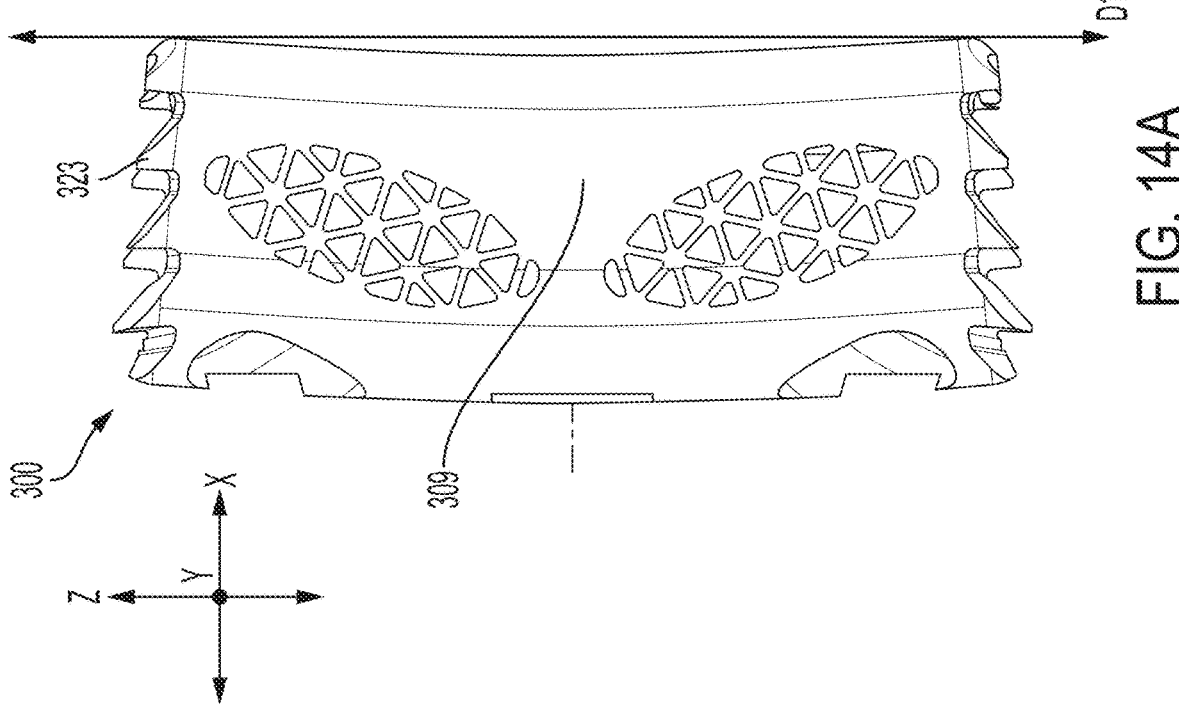
FIG. 14A is a side perspective view of the third example of a cervical corpectomy implant.

Now referring to FIGS. 14A and 14B, a side view and a top-down perspective view of cervical corpectomy implant 300 are shown. As stated above, cervical corpectomy implant 300 may have the same, similar and/or substantially the same features and functionality as explained above with respect to cervical corpectomy implant 100 or 200 for example, anti-migration feature 323 (corresponding to anti-migration features 123 and 223). In some embodiments, cervical corpectomy implant 300 may comprise interior lattice structure 325 which is configured to effectively reduce the device stiffness and improve radiolucency (x-ray effectiveness) by reducing the density of the material, as compared to solid material which requires the entire space volume to be filled with materials. In some embodiments, cervical corpectomy implant 300 may comprise an undercut along plane D1 that provides extra clearance for the spinal cord such that cervical corpectomy implant 300 may be installed conforming with the curvature of the spinal cord.

Figure 15C:
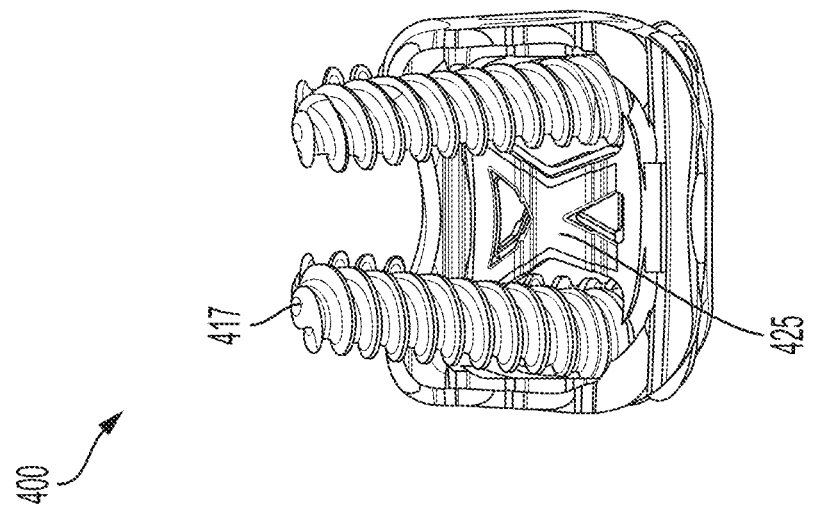
FIG. 15C is a top-down perspective view of the fourth example of a cervical corpectomy implant.
Figure 15B:
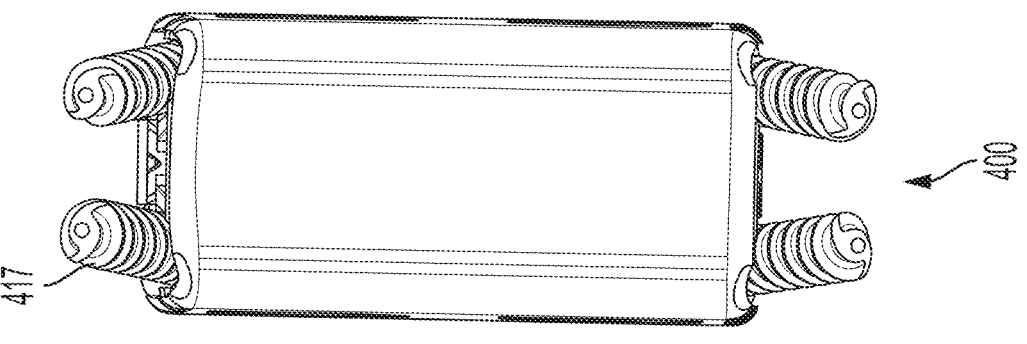
FIG. 15B is a rear perspective view of the fourth example of a cervical corpectomy implant.
Figure 15A:
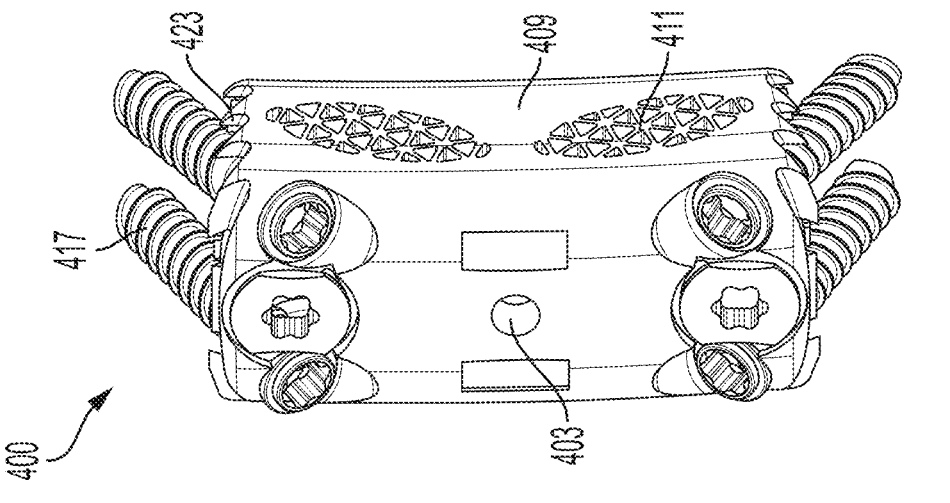
FIG. 15A is a front perspective view of the fourth example of a cervical corpectomy implant.

Now referring to FIGS. 15A-15C, a front perspective view, a rear perspective view, and a top-down perspective view of a cervical corpectomy implant 400 are shown. In various embodiments, cervical corpectomy implant 400 may have the same, similar and/or substantially the same features and functionality as explained above with respect to cervical corpectomy implant 100, 200, or 300 such as threaded hole 403 that may be configured to provide an attachment mechanism for an insertion instrument. In some embodiments, cervical corpectomy implant 400 may comprise outer shell 409 enclosing the interior implant lattice. In some embodiments, cervical corpectomy implant 400 may comprise sagittal window frame 411 to provide bone ingrowth and injection of bone graft materials. In some embodiments, cervical corpectomy implant 400 may comprise anti-migration feature(s) 423 that reduces/prevents retropulsion, or migration after the implant is inserted. In some embodiments, cervical corpectomy implant 400 may comprise further interior lattice structure 425 configured to effectively reduce the device stiffness and improve radiolucency (x-ray effectiveness). In some embodiments, cervical corpectomy implant 400 may comprise bone screw 417 that is inserted through the corpectomy implant to engage the vertebral endplates.

Figure 16A:
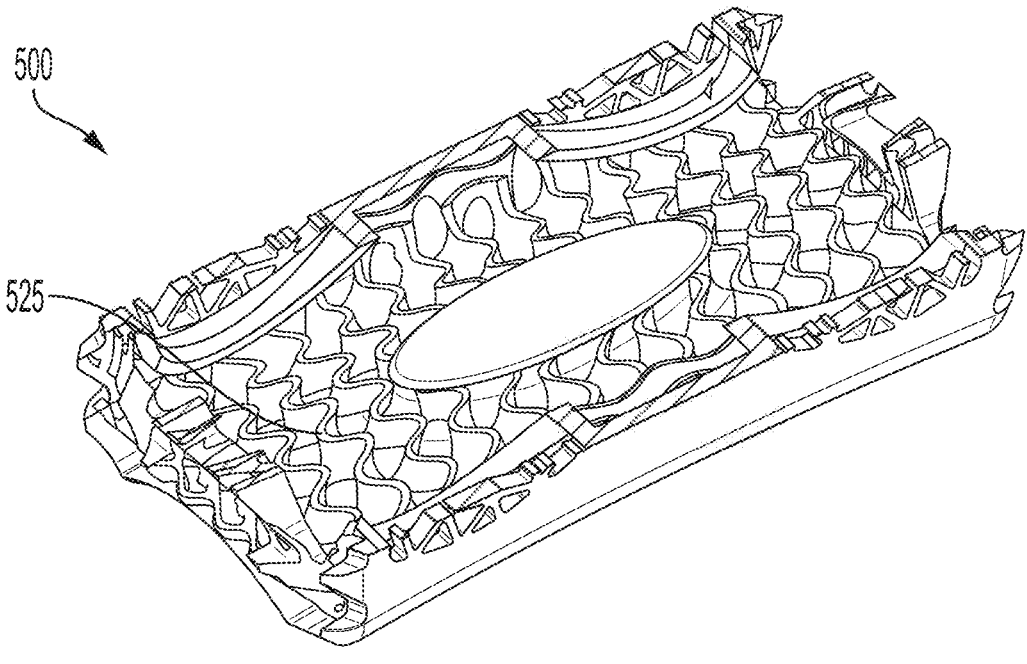
FIG. 16A is a cross-section perspective view of a cervical corpectomy implant showing an open cell lattice.
Figure 16B:
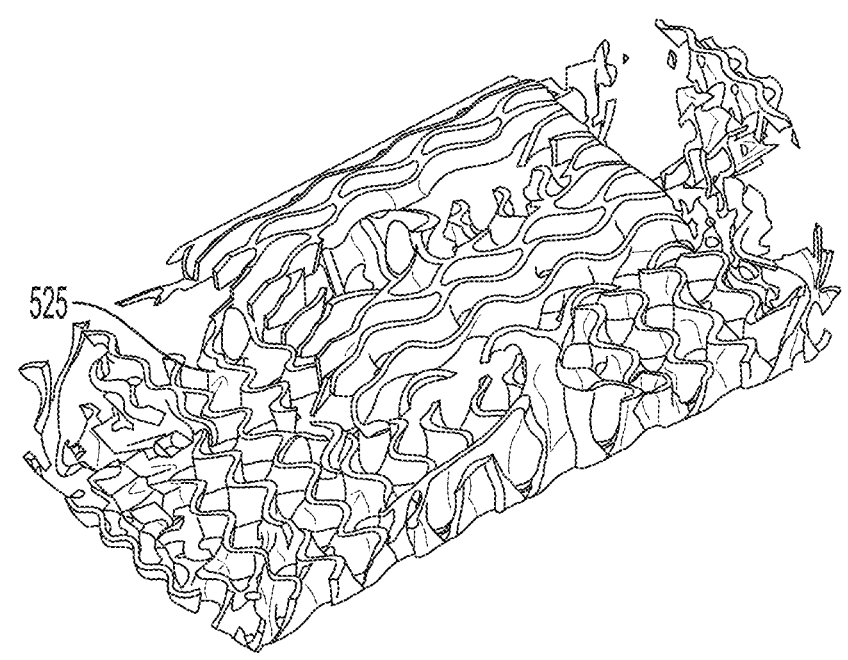
FIG. 16B is a view of the open cell lattice of the third example of a cervical corpectomy implant.

In FIGS. 16A and 16B, interior lattice structure 525 of an embodiment of cervical corpectomy implant 500 is shown. In some embodiments, cervical corpectomy implant 500 may be the same, as similar to, or substantially the same as cervical corpectomy implants 100, 200, 300 or 400. As seen in FIGS. 16A and 16B, interior lattice structure 525 may comprise an open cell lattice in a periodic, repeating structure rather than a stochastic or random lattice. In this configuration, bone growth and bone graft packing may be more uniform and evenly distributed in the periodic structure, and the interior of cervical corpectomy implant is easier to clean.

In some embodiments, any one of implants 100, 200, or 300 as disclosed in FIGS. 1-16B of may be modified to be an interbody implant, for example, for use in the disc space in the cervical spine, by reducing the height to be able to fit between the disc space. Such interbody implant would comprise the same, similar and/or substantially the same features as any one of implants as disclosed in FIGS. 1-16B. In some embodiments, any one of implants 100, 200, or 300 may be modified along various planes, e.g., X-Y, Y-Z, or X-Z, to accommodate various cavity size of adjacent boney structures between vertebrae in a patient's spine. In some embodiments, any one of implants 100, 200, or 300 may be modified to include more or less porosity within the stochastic lattice structure, graft hole (e.g., 105) or lateral holes (e.g., 113) to accommodate diffusion of various therapeutic agents, including but not limited to bone graft material, therapeutic polynucleotides and/or growth promoting material, to facilitate the fusion of damaged vertebrae.

In some embodiments, any one of cervical corpectomy implant disclosed in this document may be used to treat a plurality of vertebrae regions in a patient. In some embodiment, the method may comprise inserting a cervical corpectomy implant of the present disclosure between an upper and lower vertebrae. In some embodiments, the cervical corpectomy implant may comprise a structural volume comprising; an anterior volume comprising a first lattice structure, a posterior volume comprising a second lattice structure, a first side volume comprising a third lattice structure, and a second side volume comprising a fourth lattice structure, an upper endplate volume comprising a fifth lattice structure; and a lower endplate volume comprising a sixth lattice structure.

In some embodiments, one or more of the first lattice structure, the second lattice structure, the third lattice structure, the fourth lattice structure, the fifth lattice structure, and the sixth lattice structures may be stochastic. In some embodiments, the anterior volume, the posterior volume, the first side volume, the second side volume, the upper endplate volume, and the lower endplate volume may each have an average lattice pore size of about 100 to about 500 microns. In some embodiments, the anterior volume, the posterior volume, the first side volume, and the second side volume may be arranged to form a hollow cavity extending along an axis between the upper endplate volume and the lower endplate volume. In some embodiments, the upper endplate volume may comprise a first plurality of anti-migration features extending from upper endplate volume surface, and the lower endplate volume may comprise a second plurality of anti-migration features extending from lower endplate volume surface.

In some embodiments the method may comprise attaching the upper endplate volume to the upper vertebrae in a configuration that the first plurality of anti-migration features engages with an inferior surface of the upper vertebrae; positioning the cervical corpectomy implant within a gap between the upper and the lower vertebrae; attaching the lower endplate volume to the lower vertebrae in a configuration that the second plurality of anti-migration features engages with a superior surface of the lower vertebrae. In some embodiments, the method may further comprise placing a cervical plate (e.g., 150) adjacent to the anterior volume to stabilize the cervical corpectomy implant between the upper and the lower vertebrae to prevent or restrict the movement and/or migration of the corpectomy implant post-surgery. In some embodiments, the cervical plate may be installed by inserting a first bone through the cervical plate into the upper vertebrae and inserting a second bone screw through the cervical plate into the lower vertebrae to stabilize the corpectomy implant between the upper vertebrae and the lower vertebrae. In some embodiments, the method may comprise the cervical corpectomy implant spanning more than one vertebral level.

Figure 17:
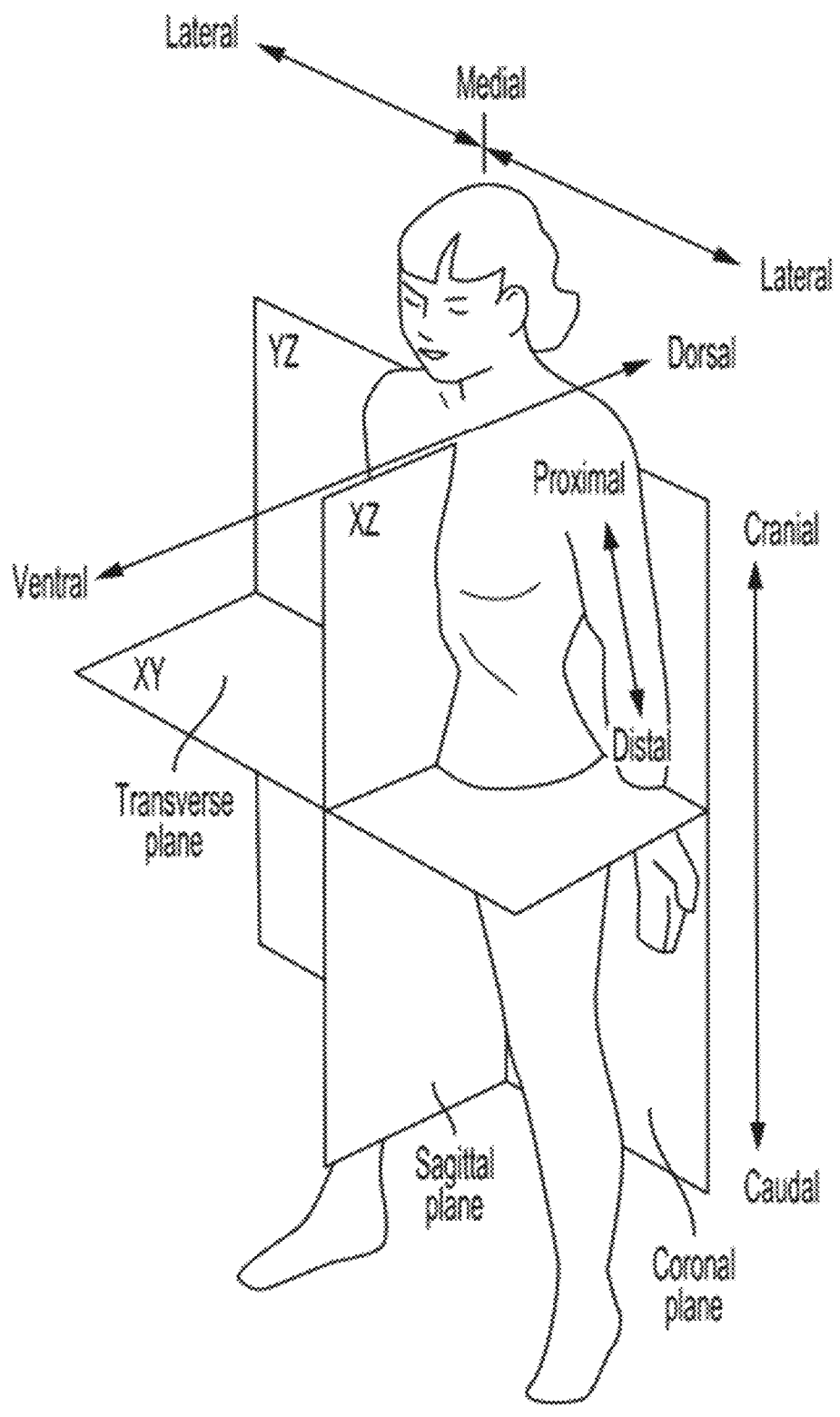
FIG. 17 is a reference diagram of various anatomical planes of a human.
Figure 18:
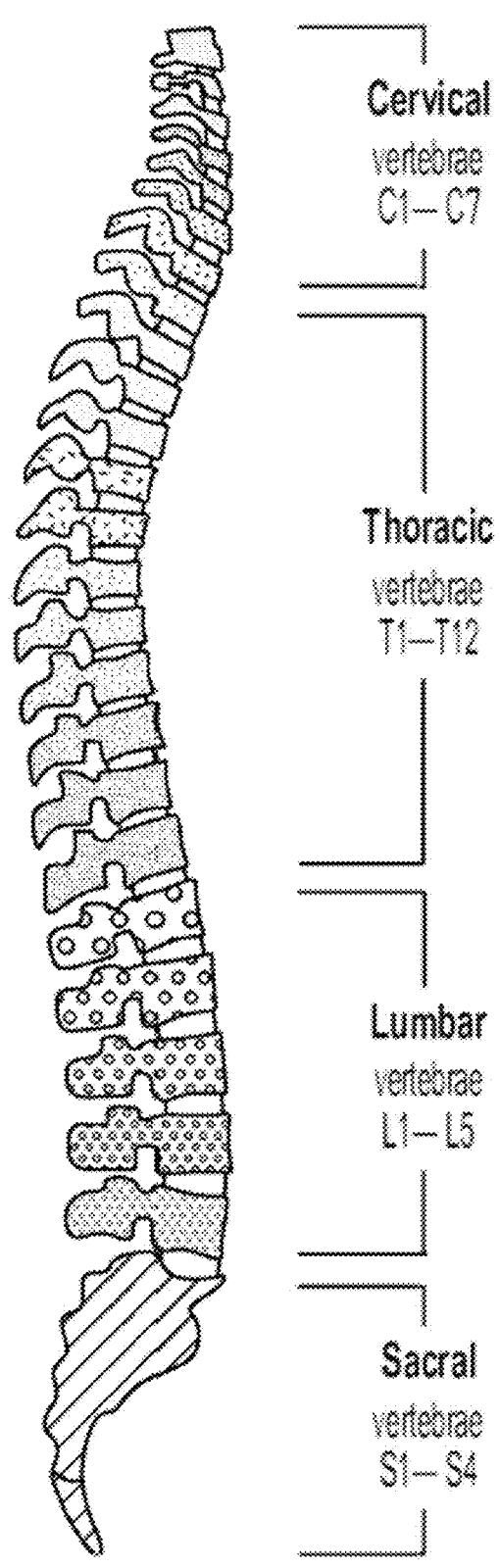
FIG. 18 is a reference diagram of a human spine.

FIG. 17 is a reference drawing showing various planes and reference directions of which the various disclosed implant embodiments may move in or act in with reference to a patient. FIG. 18 is a reference drawing showing the human spine of which various disclosed implant embodiments may be installed in. The human spine, as depicted in FIG. 17, consists of a stack of 33 curved vertebrae that are structurally divided into five regions, namely, cervical region (C1-C7), thoracic region (T1-T12), lumbar region (L1-L5) and, the fused sacrum and coccyx regions. Towards the bottom of the spine, the vertebrae are larger because the spine supports heavier loads of the body in this area. The cervical vertebrae, forming the neck area, are relatively small to promote flexibility of the head and because they support smaller loads relative to the thoracic and lumbar regions. Just below the cervical vertebrae are the thoracic vertebrae, which form the upper back. The thoracic vertebrae are larger than the cervical vertebrae and increase in size from top towards bottom. Below the thoracic region lies the lumbar vertebrae, which are even larger and support the weight of the entire upper body. Relative motion in the spine may also vary along the length of the spinal column, as the cervical vertebra have a greater range of motion than the lower lumbar vertebra.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Without excluding further possible embodiments, certain example embodiments are summarized in the following clause:

Clause 1: A cervical corpectomy implant, comprising: a structural volume comprising; an anterior volume comprising a first lattice structure, a posterior volume comprising a second lattice structure, a first side volume comprising a third lattice structure, and a second side volume comprising a fourth lattice structure, an upper endplate volume comprising a fifth lattice structure; and a lower endplate volume comprising a sixth lattice structure; wherein one or more of the first lattice structure, the second lattice structure, the third lattice structure, the fourth lattice structure, the fifth lattice structure, and the sixth lattice structures are stochastic, wherein the anterior volume, the posterior volume, the first side volume, the second side volume, the upper endplate volume, and the lower endplate volume each have an average lattice pore size of about 100 to about 500 microns, wherein the anterior volume, the posterior volume, the first side volume, and the second side volume are arranged to form a hollow cavity extending along an axis between the upper endplate volume and the lower endplate volume, wherein the upper endplate volume comprises a first plurality of anti-migration features extending from upper endplate volume surface, and wherein the lower endplate volume comprises a second plurality of anti-migration features extending from lower endplate volume surface.

Clause 2: The cervical corpectomy implant of clause 1, wherein the anterior volume, the posterior volume, the first side volume, the second side volume, the upper endplate volume, and the lower endplate volume each have a porosity from about 30% to about 70%.

Clause 3: The cervical corpectomy implant of clause 2, wherein the upper endplate volume and the lower endplate volume comprise greater porosity compared to the anterior volume, the posterior volume, the first side volume, and the second side volume.

Clause 4: The cervical corpectomy implant of any one of preceding clauses, wherein the anterior volume, the posterior volume, the first side volume, the second side volume, the upper endplate volume, and the lower endplate volume each have a volume fill % from about 50% to about 99%, based on the total volume space occupied by the first lattice structure, the second lattice structure, the third lattice structure, the fourth lattice structure, the fifth lattice structure, and the sixth lattice structure, respectively.

Clause 5: The cervical corpectomy implant of clause 4, wherein the anterior volume, the posterior volume, the first side volume, and the second side volume comprise the same volume fill %.

Clause 6: The cervical corpectomy implant of clause 4, wherein the upper endplate volume and the lower endplate volume comprise the same volume fill %.

Clause 7: The cervical corpectomy implant of clause 4, wherein the upper endplate volume and the lower endplate volume comprise a lower volume fill % compared to the anterior volume fill %, the posterior volume fill %, the first side volume fill %, and the second side volume fill %.

Clause 8: The cervical corpectomy implant of any one of preceding clauses, wherein the anterior volume, the posterior volume, the first side volume, the second side volume, the upper endplate volume, and the lower endplate volume each have a uniform lattice density.

Clause 9: The cervical corpectomy implant of any one of preceding clauses, wherein one or more of the anterior volume, the posterior volume, the first side volume, or the second side volume have a lattice density gradient along a direction extending from the lower endplate volume to the upper endplate volume.

Clause 10: The cervical corpectomy implant of any one of preceding clauses, wherein the first side volume and the second side volume each comprise a plurality of lateral holes.

Clause 11: The cervical corpectomy implant of any one of preceding clauses, wherein the anterior volume comprises a threaded hole configured to attach to an insertion instrument and/or one or more graft holes configured for insertion of bone graft materials.

Clause 12: The cervical corpectomy implant of any one of preceding clauses, further comprising a solid frame that partially encloses one or more of the anterior volume, the posterior volume, the upper endplate volume, and the lower endplate volume.

Clause 13: The cervical corpectomy implant of clause 12, wherein the solid frame partially encloses the anterior volume, the posterior volume, the upper endplate volume, and the lower endplate volume.

Clause 14: The cervical corpectomy implant of clause 12, wherein the solid frame partially encloses the upper endplate volume and the lower endplate volume.

Clause 15: The cervical corpectomy implant of clause 12, wherein the solid frame partially encloses the upper endplate volume and the lower endplate volume.

Clause 16: The cervical corpectomy implant of any one of preceding clauses, wherein the anti-migration feature is a teeth structure, and wherein the teeth structure comprises a triangular structure with a shallow angle incline configured to facilitate insertion of the cervical corpectomy implant and a steep angle incline configured to suppress migration of the cervical corpectomy implant.

Clause 17: The cervical corpectomy implant of clause 17, wherein the shallow angle incline ranges from about 5° to about 40° and the steep angle incline ranges from about 50° to about 85°.

Clause 18: The cervical corpectomy implant of any one of preceding clauses, further comprising: a first chamfered edge at an intersection of the anterior volume and the upper endplate volume, and a second chamfered edge at an intersection of the anterior volume and the lower endplate volume, wherein the first chamfered edge and the second chamfered edge are each inclined at an angle from about 15° to about 60°.

Clause 19: A method for treating a plurality of vertebrae regions in a patient, the method comprising: inserting a cervical corpectomy implant between an upper and lower vertebrae, wherein the cervical corpectomy implant comprises: a structural volume comprising; an anterior volume comprising a first lattice structure, a posterior volume comprising a second lattice structure, a first side volume comprising a third lattice structure, and a second side volume comprising a fourth lattice structure, an upper endplate volume comprising a fifth lattice structure; and a lower endplate volume comprising a sixth lattice structure; wherein one or more of the first lattice structure, the second lattice structure, the third lattice structure, the fourth lattice structure, the fifth lattice structure, and the sixth lattice structures are stochastic, wherein the anterior volume, the posterior volume, the first side volume, the second side volume, the upper endplate volume, and the lower endplate volume each have an average lattice pore size of about 100 to about 500 microns, wherein the anterior volume, the posterior volume, the first side volume, and the second side volume are arranged to form a hollow cavity extending along an axis between the upper endplate volume and the lower endplate volume, wherein the upper endplate volume comprises a first plurality of anti-migration features extending from upper endplate volume surface, and wherein the lower endplate volume comprises a second plurality of anti-migration features extending from lower endplate volume surface, attaching the upper endplate volume to the upper vertebrae in a configuration that the first plurality of anti-migration features engages with an inferior surface of the upper vertebrae; positioning the cervical corpectomy implant within a gap between the upper and the lower vertebrae; attaching the lower endplate volume to the lower vertebrae in a configuration that the second plurality of anti-migration features engages with a superior surface of the lower vertebrae; placing a cervical plate adjacent to the anterior volume; inserting a first bone through the cervical plate into the upper vertebrae and inserting a second bone screw through the cervical plate into the lower vertebrae to stabilize the corpectomy implant between the upper vertebrae and the lower vertebrae.

Clause 20: The method of clause 19, wherein the positioning comprises the cervical corpectomy implant spanning more than one vertebral level.

What is claimed is:

1. A cervical corpectomy implant, comprising:
a structural volume comprising;
    an anterior volume comprising a first lattice structure,
    a posterior volume comprising a second lattice structure,
    a first side volume comprising a third lattice structure, and
    a second side volume comprising a fourth lattice structure,
an upper endplate volume comprising a fifth lattice structure; and
a lower endplate volume comprising a sixth lattice structure;
    wherein one or more of the first lattice structure, the second lattice structure, the third lattice structure, the fourth lattice structure, the fifth lattice structure, and the sixth lattice structures are stochastic,
    wherein the upper endplate volume and the lower endplate volume comprise different volume fill % compared to the anterior volume, the posterior volume, the first side volume, and the second side volume,
    wherein the anterior volume, the posterior volume, the first side volume, the second side volume, the upper endplate volume, and the lower endplate volume each have an average lattice pore size of about 100 to about 500 microns,
    wherein the anterior volume, the posterior volume, the first side volume, and the second side volume are arranged to form a hollow cavity extending along an axis between the upper endplate volume and the lower endplate volume,
    wherein the upper endplate volume comprises a first plurality of anti-migration features extending from upper endplate volume surface, and
    wherein the lower endplate volume comprises a second plurality of anti-migration features extending from lower endplate volume surface.

2. The cervical corpectomy implant of claim 1, wherein the anterior volume, the posterior volume, the first side volume, the second side volume, the upper endplate volume, and the lower endplate volume each have a porosity from about 30% to about 70%.

3. The cervical corpectomy implant of claim 2, wherein the upper endplate volume and the lower endplate volume comprise greater porosity compared to the anterior volume, the posterior volume, the first side volume, and the second side volume.

4. The cervical corpectomy implant of claim 1, wherein the anterior volume, the posterior volume, the first side volume, the second side volume, the upper endplate volume, and the lower endplate volume each have a volume fill % from about 50% to about 99%, based on the total volume space occupied by the first lattice structure, the second lattice structure, the third lattice structure, the fourth lattice structure, the fifth lattice structure, and the sixth lattice structure, respectively.

5. The cervical corpectomy implant of claim 4, wherein the anterior volume, the posterior volume, the first side volume, and the second side volume comprise the same volume fill %.

6. The cervical corpectomy implant of claim 4, wherein the upper endplate volume and the lower endplate volume comprise a lower volume fill % compared to the anterior volume fill %, the posterior volume fill %, the first side volume fill %, and the second side volume fill %.

7. The cervical corpectomy implant of claim 1, wherein the anterior volume, the posterior volume, the first side volume, the second side volume, the upper endplate volume, and the lower endplate volume each have a uniform lattice density.

8. The cervical corpectomy implant of claim 1, wherein one or more of the anterior volume, the posterior volume, the first side volume, or the second side volume have a lattice density gradient along a direction extending from the lower endplate volume to the upper endplate volume.

9. The cervical corpectomy implant of claim 1, wherein the first side volume and the second side volume each comprise a plurality of lateral holes.

10. The cervical corpectomy implant of claim 1, wherein the anterior volume comprises a threaded hole configured to attach to an insertion instrument and/or one or more graft holes configured for insertion of bone graft materials.

11. The cervical corpectomy implant of claim 1, further comprising a solid frame that partially encloses one or more of the anterior volume, the posterior volume, the upper endplate volume, and the lower endplate volume.

12. The cervical corpectomy implant of claim 11, wherein the solid frame partially encloses the anterior volume, the posterior volume, the upper endplate volume, and the lower endplate volume.

13. The cervical corpectomy implant of claim 11, wherein the solid frame partially encloses the upper endplate volume and the lower endplate volume.

14. The cervical corpectomy implant of claim 1, wherein the anti-migration feature is selected from a teeth structure, a conical structure, or a combination thereof.

15. The cervical corpectomy implant of claim 1, wherein the anti-migration feature is a teeth structure, and wherein the teeth structure comprises a triangular structure with a shallow angle incline configured to facilitate insertion of the cervical corpectomy implant and a steep angle incline configured to suppress migration of the cervical corpectomy implant.

16. The cervical corpectomy implant of claim 15, wherein the shallow angle incline ranges from about 50 to about 400 and the steep angle incline ranges from about 500 to about 850.

17. The cervical corpectomy implant of claim 1, further comprising:
    a first chamfered edge at an intersection of the anterior volume and the upper endplate volume, and
    a second chamfered edge at an intersection of the anterior volume and the lower endplate volume,
    wherein the first chamfered edge and the second chamfered edge are each inclined at an angle from about 15° to about 60°.

18. A method for treating a plurality of vertebrae regions in a patient, the method comprising:
    inserting a cervical corpectomy implant between an upper and lower vertebrae, wherein the cervical corpectomy implant comprises:
        a structural volume comprising;
            an anterior volume comprising a first lattice structure,
            a posterior volume comprising a second lattice structure,
            a first side volume comprising a third lattice structure, and a second side volume comprising a fourth lattice
structure,
an upper endplate volume comprising a fifth lattice
structure; and
a lower endplate volume comprising a sixth lattice
structure;
wherein one or more of the first lattice structure, the
second lattice structure, the third lattice structure, the
fourth lattice structure, the fifth lattice structure, and
the sixth lattice structures are stochastic,
wherein the upper endplate volume and the lower
endplate volume comprise different volume fill %
compared to the anterior volume, the posterior vol-
ume, the first side volume, and the second side
volume,
wherein the anterior volume, the posterior volume, the
first side volume, the second side volume, the upper
endplate volume, and the lower endplate volume
each have an average lattice pore size of about 100
to about 500 microns,
wherein the anterior volume, the posterior volume, the
first side volume, and the second side volume are
arranged to form a hollow cavity extending along an
axis between the upper endplate volume and the
lower endplate volume,
wherein the upper endplate volume comprises a first
plurality of anti-migration features extending from
upper endplate volume surface, and wherein the lower endplate volume comprises a second
plurality of anti-migration features extending from
lower endplate volume surface, and
attaching the upper endplate volume to the upper verte-
brae in a configuration that the first plurality of anti-
migration features engages with an inferior surface of
the upper vertebrae;
positioning the cervical corpectomy implant within a gap
between the upper and the lower vertebrae;
attaching the lower endplate volume to the lower verte-
brae in a configuration that the second plurality of
anti-migration features engages with a superior surface
of the lower vertebrae;
placing a cervical plate adjacent to the anterior volume;
inserting a first bone screw through the cervical plate into
the upper vertebrae and inserting a second bone screw
through the cervical plate into the lower vertebrae to
stabilize the corpectomy implant between the upper
vertebrae and the lower vertebrae.

19. The method of claim 18, wherein the positioning
comprises the cervical corpectomy implant spanning more
than one vertebral level.

20. The method of claim 18, wherein the cervical plate
does not engage with the cervical corpectomy implant.

* * * * *